(12) United States Patent
Barkin et al.

(10) Patent No.: US 12,239,824 B2
(45) Date of Patent: Mar. 4, 2025

(54) NEEDLE-FREE INJECTOR WITH GAS BUBBLE DETECTION

(71) Applicant: PORTAL INSTRUMENTS, INC., Cambridge, MA (US)

(72) Inventors: Tyler F. Barkin, Cambridge, MA (US); Marc Pelletier, Cambridge, MA (US)

(73) Assignee: Portal Instruments, Inc., Cambridge, MA (US)

( * ) Notice: Subject to any disclaimer, the term of this patent is extended or adjusted under 35 U.S.C. 154(b) by 1145 days.

(21) Appl. No.: 17/013,105

(22) Filed: Sep. 4, 2020

(65) Prior Publication Data

US 2021/0146050 A1    May 20, 2021

Related U.S. Application Data

(60) Provisional application No. 62/896,395, filed on Sep. 5, 2019.

(51) Int. Cl.
*A61M 5/30*    (2006.01)

(52) U.S. Cl.
CPC ........... *A61M 5/30* (2013.01); *A61M 2205/52* (2013.01); *A61M 2205/8206* (2013.01)

(58) Field of Classification Search
CPC ............... A61M 5/30; A61M 2205/52; A61M 2205/8206; A61M 5/155; A61M 5/2046; A61M 11/02
See application file for complete search history.

(56) References Cited

U.S. PATENT DOCUMENTS

| 6,994,127 B2 | 2/2006 | Neracher |
| 2005/0154346 A1 | 7/2005 | Green |

(Continued)

FOREIGN PATENT DOCUMENTS

| CA | 1184821 | 4/1985 |
| CA | 2164582 | 6/1996 |

(Continued)

OTHER PUBLICATIONS

International Search Report, corresponding PCT/US2020/049517, dated Oct. 23, 2020.

(Continued)

*Primary Examiner* — Lauren P Farrar
(74) *Attorney, Agent, or Firm* — Strategic Patents, P.C.

(57) ABSTRACT

A needle-free injector includes a housing, a cartridge positioned within the housing, and a plunger slidably coupled to and disposed within the chamber, a motor operatively coupled to the plunger, the motor operable to actuate the plunger in the chamber, and a controller operatively coupled to the motor. The controller is operable to selectively operate the plunger according to any of a first delivery profile, a second delivery profile, and a third delivery profile. The controller may transition from the first delivery profile to the second delivery profile responsive to compression of a gas in the chamber, e.g., upon detecting a spike in a measured current applied to the motor. The controller may transition from the second delivery profile to the third delivery profile responsive to detecting a steady state condition between the measured current and a velocity of the plunger. Methods of delivering an injectate using the needle-free injectors are provided. Methods of facilitating needle-free injection of an injectate using the needle-free injectors are also provided.

20 Claims, 16 Drawing Sheets

(56) References Cited

U.S. PATENT DOCUMENTS

| | | | |
|---|---|---|---|
| 2008/0119783 A1* | 5/2008 | Green | A61M 5/30 604/68 |
| 2019/0046727 A1* | 2/2019 | Aneas | A61M 5/20 |
| 2019/0076602 A1 | 3/2019 | Dyer et al. | |
| 2019/0247577 A1 | 8/2019 | Consiglio et al. | |

FOREIGN PATENT DOCUMENTS

| | | |
|---|---|---|
| CA | 2444275 | 10/2002 |
| CA | 2630686 | 5/2007 |
| CA | 2666755 | 3/2008 |
| CA | 2756118 | 9/2010 |
| CA | 2987866 | 3/2012 |
| CA | 2811865 | 4/2012 |
| CA | 2821850 | 6/2012 |
| CA | 2905087 | 9/2014 |
| CA | 2931006 | 7/2015 |
| CA | 3069716 | 8/2016 |
| CA | 3075748 | 3/2019 |
| WO | 02/49697 A1 | 6/2002 |

OTHER PUBLICATIONS

CIPO, "CA Application No. 3,153,428, "Examiner's Report" dated Mar. 28, 2024", 5 pages.

CNIPA, "CN Application No. 202080073179.7 Office Action mailed Mar. 30, 2024", 7 pages.

EPO, , "PCT Application No. PCT/US2020/049517, "International Preliminary Report on Patentability," dated Mar. 17, 2022,", , 10 pages.

EPO, "EP Application No. 20775525.7 Communication Pursuant to Article 94(3) mailed Sep. 2, 2024", 3 pages.

CNIPA, "CN Application No. 202080073179.7 Second Office Action mailed Nov. 22, 2024", 4 pages.

* cited by examiner

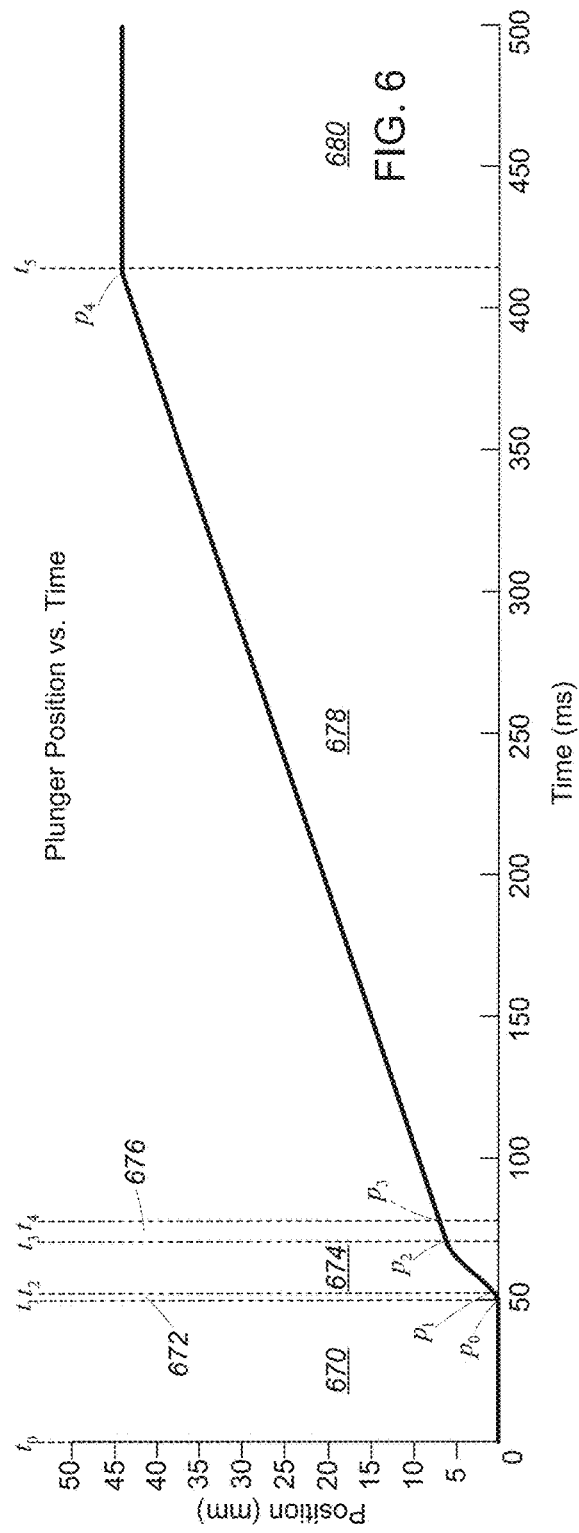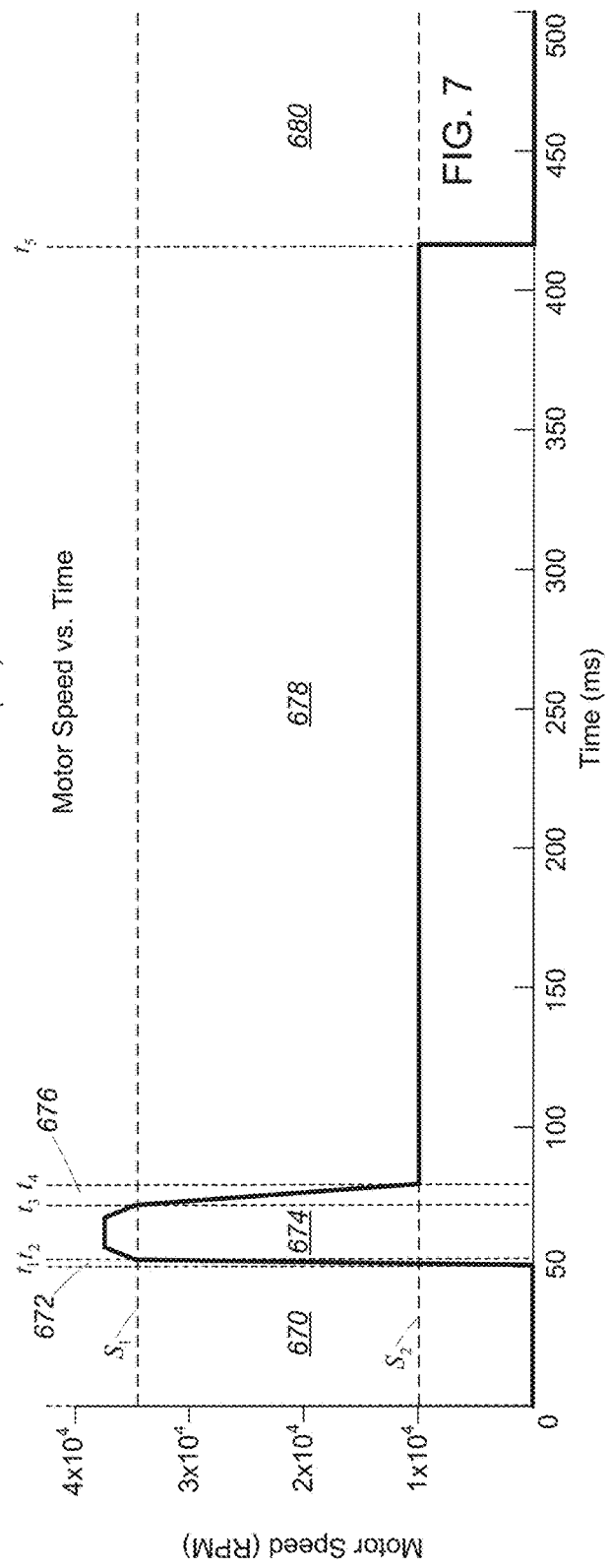

$$\theta(t) = \theta_0 - \frac{C_1}{C_2} \cdot \left(\frac{F}{C_2} - \omega_0\right) + \frac{C_1}{C_2} \cdot \left(\frac{F}{C_2} - \omega_0\right) \cdot e - \frac{C_2}{C_1} \cdot t + \frac{F}{C_2} \cdot t$$

NEEDLE-FREE INJECTOR WITH GAS BUBBLE DETECTION

CROSS-REFERNCE TO RELATED APPLICATIONS

This application claims priority under 35 U.S.C. § 119 (e) to U.S. Provisional Patent Application Ser. No. 62/896,395 titled "Needle-Free Injector with Gas Bubble Detection" filed Sep. 5, 2019, the entire disclosure of which is hereby incorporated herein by reference in its entirety for all purposes.

BACKGROUND

This disclosure relates to a needle-free transdermal injection device.

In the field of modern medicine, drugs are often delivered through the skin into the bloodstream of patients. Traditionally, this is accomplished by insertion of a needle through the patient's skin and into a target area for an injection. However, the use of needles presents significant drawbacks ranging from patient fear and discomfort to safety hazards associated with handling used needles.

Needle-free transdermal injection devices have been developed as an alternative to needle-based injectors. These devices typically use a high pressure, narrow jet of injectate to penetrate a patient's skin, obviating the need to pierce the patient's skin with a needle. However, there remains a need for improved needle-free injection devices.

SUMMARY

A needle-free injector monitors the compression of a volume of gas within a cartridge of an injectate during operating of a plunger according to a first delivery profile. When the volume of gas becomes sufficiently compressed (as measured by a spike in measured current applied to the motor of the needle-free injector), operation of the needle-free injector is transitioned to operate according to a second delivery profile. Operation according to the second deliver profile produces an injectate velocity sufficient to penetrate a permeable barrier. Once the injectate has penetrated the permeable barrier and a steady state condition has been reached, operation of the needle-free injector is transitioned to operate according to a third delivery profile to deliver the injectate to a subject. By detecting the gas bubble compression prior to delivery of injectate in this manner, an injection stream can be controlled to more closely reproduce a target injection profile.

In accordance with one aspect, there is provided a needle-free injector. The needle-free injector may comprise a housing, a cartridge positioned within the housing, and a plunger slidably coupled to and disposed within the chamber, and a motor operatively coupled to the plunger, the motor operable to actuate the plunger in the chamber. The plunger may be positioned to discharge the volume of the injectate through the exit port when slid within the chamber. The cartridge may include an exit port and a chamber for holding a volume of an injectate. The needle-free injector may further comprise a controller operatively coupled to the motor, the controller operable to selectively operate the plunger according to any of a first delivery profile, a second delivery profile, and a third delivery profile, the controller operable to transition from the first delivery profile to the second delivery profile responsive to detecting a spike in a measured current applied to the motor upon compression of a gas in the chamber by the plunger, the controller further operable to transition from the second delivery profile to the third delivery profile responsive to detecting a steady state condition between the measured current and a velocity of the plunger.

In some embodiments, an average velocity of the plunger during operation of the first delivery profile may be greater than an average velocity of the plunger during operation of the second delivery profile.

In some embodiments, the compression of the gas in the chamber is detected based on a drive current supplied to the motor. In some embodiments, the compression of the gas in the chamber is detected based on a position of the motor measured using a rotary encoder for the motor. In some embodiments, the compression of the gas in the chamber is detected based on an increase in force required to maintain a velocity of the motor during the first delivery profile based on a comparison of a drive current suppled to the motor with a position of the motor measured using a rotary encoder for the motor.

The injectate may comprise an injectable pharmaceutical or nutraceutical formulation. For example, the injectable pharmaceutical formulation may comprise a high viscosity biologic formulation.

In some embodiments, a plunger velocity of the second delivery profile may produce an injectate velocity sufficient for the injectate to penetrate a permeable barrier. The permeable barrier may be a skin of a subject. In particular embodiments, the injectate velocity may be from about 150 m/s to about 250 m/s.

In some embodiments, the first delivery profile may cause the plunger to operate at a velocity from about 300 m/s to about 500 m/s. In some embodiments, the second delivery profile may cause the plunger to operate at a velocity from about 60 m/s to about 150 m/s. In some embodiments, the third delivery profile may cause the plunger to operate at a velocity from about 80 m/s to about 120 m/s.

In accordance with another aspect, there is provided a needle-free injector. The needle-free injector may comprise a plunger positioned to pressurize a fluid and a gas in a cartridge having an exit port. The needle-free injector may further comprise a motor operatively coupled to the plunger. The motor may be operable to actuate the plunger in a linear motion along an axis of the cartridge to direct the fluid from the cartridge. The needle-free injector may additionally comprise a controller operatively coupled to the motor. The controller may be operable to, responsive to an injection initiation signal, operate the plunger according to a first delivery profile to compress the gas within the cartridge and operate the plunger according to a second delivery profile responsive to detecting a compression of the gas in the cartridge above a predetermined threshold.

In some embodiments, detecting the compression of the gas in the cartridge above the predetermined threshold may comprise detecting a deviation in a motor current between a free-running drive current predicted by a model and the measured current supplied to the motor. In some embodiments, detecting the compression of the gas in the cartridge includes detecting an increase in a motor current above a predetermined threshold for maintaining a velocity of the plunger within the first delivery profile. In some embodiments, detecting the compression of the gas in the cartridge may comprise detecting a decrease in a velocity of the plunger below a predetermined threshold. In some embodiments, detecting the compression of the gas in the cartridge may comprise detecting a concurrent decrease in velocity of the plunger and increase in drive current to the motor.

In some embodiments, the controller may actuate the plunger responsive to feedback from an encoder operatively coupled to the motor.

In some embodiments, the first delivery profile may have a first target velocity greater than a second target velocity of the second delivery profile. In some embodiments, the second delivery profile is a biphasic profile comprising a piercing phase and a delivery phase. In particular embodiments, a plunger velocity in the piercing phase may decrease as a function of time.

In accordance with another aspect, there is provided a method of delivering an injectate using a needle-free injector. The method may comprise providing a needle-free injector as described herein. The needle-free injector may comprise a housing having a cartridge for holding a chamber, a plunger constructed and arranged to direct an injectate from the chamber, and a motor operatively coupled to the plunger. The method may cause, responsive to initiating an injection with the needle-free injector, the needle-free injector to operate the plunger according to a first delivery profile, monitor a current applied to the motor during the first delivery profile, transition from the first delivery profile to the second delivery profile responsive to detecting, based at least in part on a spike in the current applied to the motor, compression of a gas in the chamber by the plunger, operate the plunger according to the second delivery profile, transition from the second delivery profile to the third delivery profile responsive to detecting a steady state condition between the measured current and a velocity of the plunger, and to operate the plunger according to the third delivery profile until a predetermined volume of the injectate has been delivered from the chamber through the exit port.

In some embodiments, transitioning from the first delivery profile to the second delivery profile may comprise transitioning from the first delivery profile to the second delivery profile upon detecting a spike in a measured current applied to the motor upon compression of the gas. In particular embodiments, transitioning from the first delivery profile to the second delivery profile may comprise decreasing the current applied to the motor to within a range of 0 A to about 10 A.

In some embodiments, operating the plunger according to the second delivery profile may comprise operating the plunger at a velocity sufficient to overcome a restoring force exerted onto the plunger to deliver the injectate through the permeable barrier. For example, operating the plunger according to the second delivery profile may comprise operating the plunger while maintaining the compression of the gas in the chamber. In some embodiments, operating the plunger according to the second delivery profile may result in the injectate velocity being sufficient to penetrate a permeable barrier, such as a skin of a subject.

In some embodiments, operating the plunger in the third delivery profile may comprise adjusting the velocity of the plunger as the injectate is delivered. For example, operating the plunger in the third delivery profile may comprise decreasing the velocity of the plunger as the injectate is delivered.

In accordance with another aspect, there is provided a method of facilitating needle-free injection of an injectate. The method may comprise providing a needle-free injector as described herein. The needle-free injector may comprise a motor operatively coupled to a plunger and a controller. The provided controller may be operable to operate the plunger in a first delivery profile, monitor a current applied to the motor during the first delivery profile, transition from the first delivery profile to the second delivery profile responsive to detecting, based at least in part on a spike in the current applied to the motor, compression of a gas in the chamber by the plunger, operate the plunger in the second delivery profile, transition from the second delivery profile to the third delivery profile responsive to detecting a steady state condition between the measured current and a velocity of the plunger, and to operate the plunger according to the third delivery profile until a predetermined volume of the injectate has been delivered from the chamber through the exit port.

In further embodiments, the method may comprise providing instructions to a user for loading a cartridge of the injectate into the needle-free injector.

In further embodiments, the method may comprise providing instructions to a user for operating the needle-free injector.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6 is a target displacement profile.

FIG. 7 is a rotary motor speed profile associated with the target displacement profile of FIG. 6.

DETAILED DESCRIPTION

In the following document, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated, and each separate value within such a range is incorporated into the specification as if it were individually recited herein. The words "about," "approximately" or the like, when accompanying a numerical value or physical property, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose or the like. Ranges of values and/or numeric values are provided herein as examples only, and do not constitute a limitation on the scope of the described embodiments unless explicitly stated otherwise. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms.

1 Needle-Free Transdermal Injection Device

Figure 1:
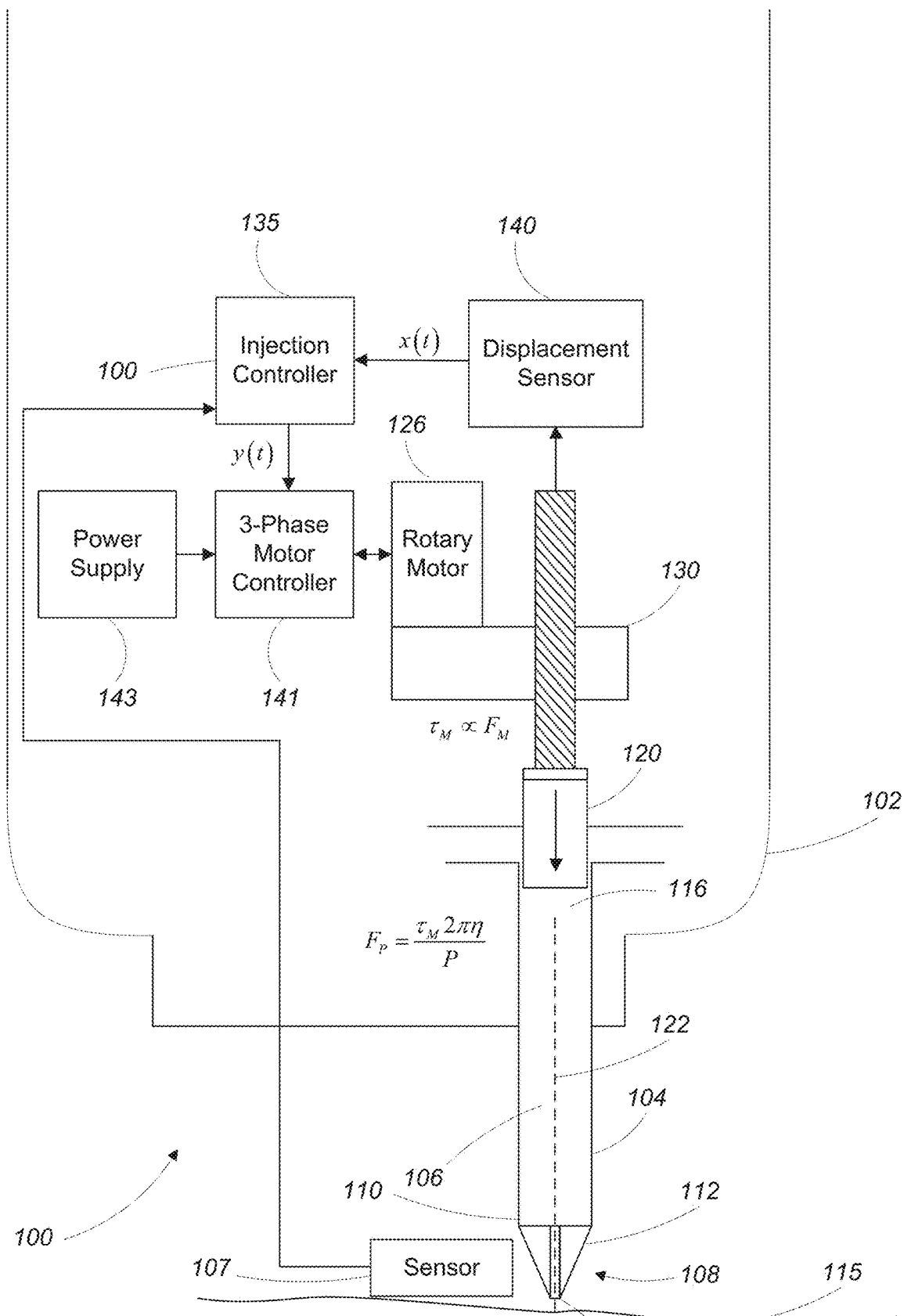
FIG. 1 is a schematic diagram of a controllable, needle-free transdermal injection device.

Referring to FIG. 1, a controllable, needle-free transdermal injection device 100 for transferring an injectate (e.g., a drug or a vaccine in any one of a number of states such as a liquid state or a powder state) through the skin of a patient includes a needle-free transdermal injector head 104 extending from a housing 102. The injector head 104 includes a chamber 106 for holding the injectate and a nozzle 108 disposed at a distal end 110 of the injector head 104. The nozzle 108 includes a head 112 and an opening 114 from which a jet of the injectate is discharged from the chamber 106. In operation, the opening 114 is placed near or against the skin 115 when the injectate is discharged.

The dimensions of the nozzle 108 may be adapted to control a shape and pressure profile of a stream of injectate exiting the nozzle 108. For example, the inner diameter of the opening 114 may be in a range of 50 μm to 300 μm, and may employ a taper along the longitudinal axis 122 toward the opening to shape an exiting stream of injectate. It will also be appreciated that the geometry of the chamber 106 relative to the opening 114 may affect how linear motion of a plunger or the like within the chamber 106 translates into an exit velocity or pressure by an injectate through the opening 114. An outer diameter of the head 112 of the nozzle 108 may narrow to the opening 114, or may remain uniform or may expand to provide a suitable resting surface for the head 112 of the nozzle 108. The nozzle 108 may have a length along the longitudinal axis 122 of about 500 μm to about 5 mm. Similarly, the chamber 106 may have any suitable length along the longitudinal axis for containing an injectate, and for displacing the injectate through the opening 114 in one or more needle-free injections.

The chamber 106 may have a proximal end 116 and a distal end 110. An actuator (i.e., a piston or plunger 120) may be slidably disposed within the chamber 106. Movement of the plunger 120 along a longitudinal axis 122 in either direction can affect the pressure within chamber 106. In some embodiments, the chamber 106 is integral to the device 100. In other embodiments, the chamber 106 is separately attachable to device 100.

In some examples, the injection device 100 includes a sensor 107 (e.g., a mechanical sensor or a capacitive sensor) for detecting a contact between the apparatus and the skin of a patient. In some examples, the sensor 107 is configured to detect an angle of the cartridge relative to the skin of the patient. In some examples, the sensor 107 is configured to detect a position of the injection opening relative to the patient's skin 115 or body. In some examples, the sensor 107 communicates with the injection controller 100 to prevent injection from occurring when the apparatus is not in contact with the patient's skin 115 or when an angle or position of the apparatus relative to the patient is incorrect.

1.1 Rotary Motor

The injection device 100 may include an electromagnetic rotary motor 126 that applies a force to the plunger 120 via a linkage 130 to inject the injectate in the chamber 106 through the skin 115. The linkage may include a ball screw actuator 130, and the linkage may also or instead include any other suitable mechanical coupling for transferring a rotary force of the rotary motor 126 into a linear force suitable for displacing injectate from the chamber 106. For example, the linkage may include one or more of lead screws, linear motion bearings, and worm drives, or another other suitable mechanical components or combination of mechanical components. As noted above, linear motion may usefully be inferred from rotation of a lead screw or the like, and the injection device 100 may be instrumented to monitor rotation in order to provide feedback on a position of the plunger 120 to a controller during an injection.

Figure 2:
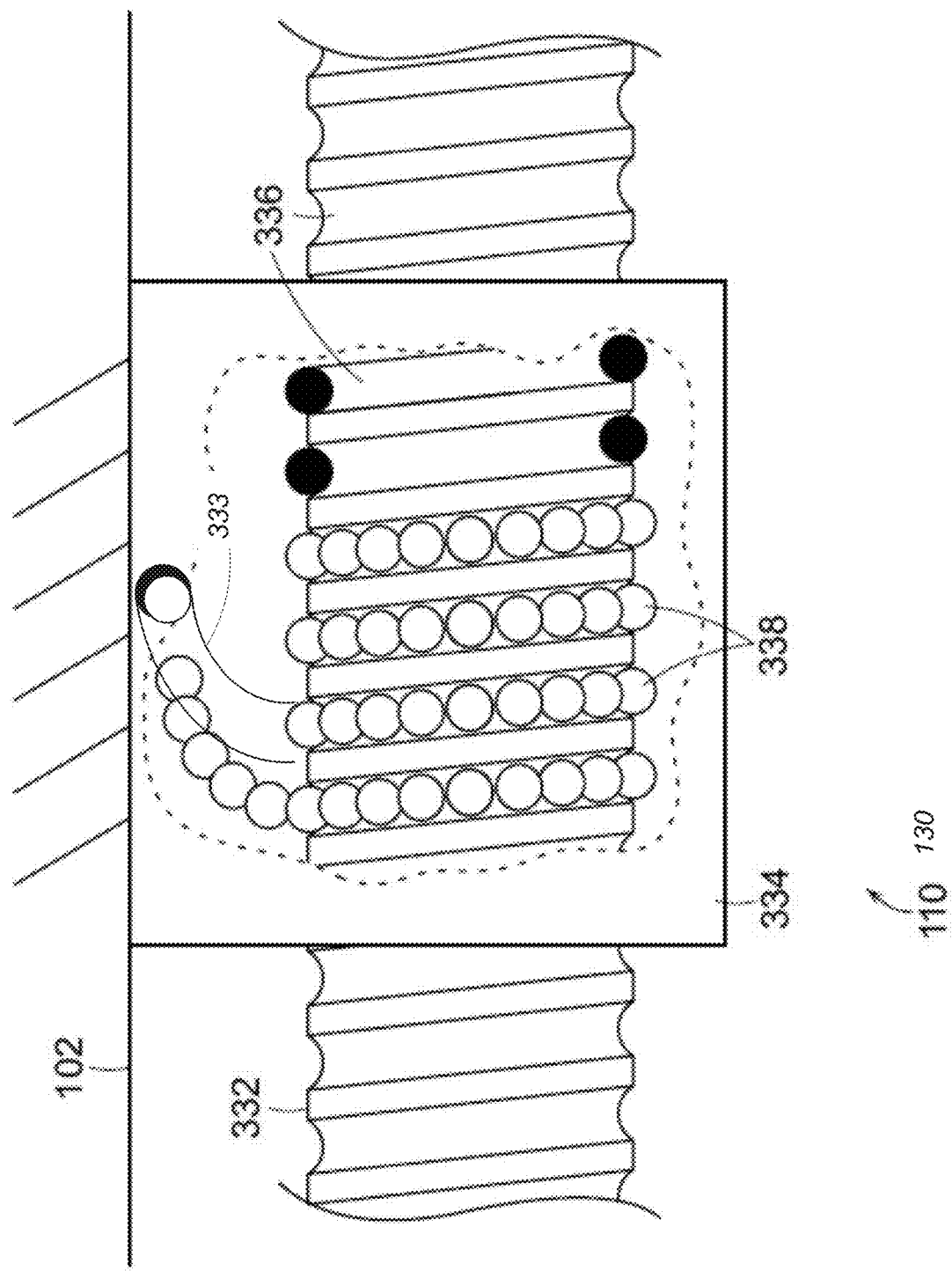
FIG. 2 is a cut-away diagram of a ball screw actuator.

Referring to FIG. 2, one example of a ball screw actuator 130 includes a screw 332 and a nut 334 (which is coupled to the housing 102 in FIG. 1), each with matching helical grooves 336. The ball screw actuator 130 may include a recirculating ball screw with a number of miniature balls 338 or similar bearings or the like that recirculate through the grooves 336 and provide rolling contact between the nut 334 and the screw 332. The nut 334 may include a return system 333 and a deflector (not shown) which, when the screw 332 or nut 334 rotates, deflects the miniature balls 338 into the return system. The balls 338 travel through the return system to the opposite end of the nut 334 in a continuous path. The balls 338 then exit from the ball return system into the grooves 336. In this way, the balls 338 continuously recirculate in a closed circuit as the screw 332 moves relative to the nut 334.

In some examples, the rotary motor 126 is of a type selected from a variety of rotational electrical motors (e.g., a brushless DC motor). The rotary motor 126 is configured to move the screw 332 of the ball screw actuator 130 back and forth along the longitudinal axis 122 by applying a torque (i.e., $\tau_M$) to either the screw 332 or the nut 334 of the ball screw actuator. The torque causes rotation of either the screw 332 or the nut 334, which in turn causes an input force $F_M(t)$, which is proportional to the torque applied by the motor, to be applied to the screw 332.

The torque $\tau_M$ applied to the screw 332 causes application of a force $F_P$ to the plunger 120 which in turn causes movement of the plunger 120 along the longitudinal axis 122. The force $F_P$ is determined according to the following equation representing an idealized relationship between torque and force for a ball screw actuator:

$$F_P = \frac{\tau_M 2\pi\eta}{P}$$

where $F_P$ is a force applied to the plunger 120 by the screw 332, $\tau_M$ is a torque applied to the screw 332, $\eta$ is an efficiency of the ball screw actuator 130, and P is a lead of the screw 332.

1.2 Control Loop

Referring again to FIG. 1, the transdermal injection device 100 may include a displacement sensor 140, an injection controller 135, and a three-phase motor controller 141. In general, the displacement sensor 140 measures a displacement x(t) of the screw 332 of the ball screw actuator 130 and/or the plunger 120. The displacement sensor 140 may, for example, measure an incremental displacement of the screw 332 by storing an initial displacement value (i.e., x(0)) and monitoring a deviation from the starting value over time. In other examples, the displacement sensor 140 measures an absolute displacement of the screw 332 relative to a position of the displacement sensor 140 or some other fixed reference point. In another aspect, the displacement sensor 140 may be coupled to a nut or other component of a ball screw that controls linear movement. In this configuration, the displacement sensor 140 can measure rotation of the screw drive, and rotational motion may be computationally converted into linear displacement for purposes of controlling operation of the device 100.

The displacement x(t) measured by (or calculated using data from) the displacement sensor 140 may be provided as input to the injection controller 135. As is described in greater detail below, the injection controller 135 processes the displacement x(t) to determine a motor control signal y(t). The motor control signal y(t) is provided to the three-phase motor controller 141 which, in conjunction with a power supply 143, drives the rotary motor 126 according to the motor control signal y(t). The motor 126 causes the torque $\tau_M(t)$ to be applied to the screw 332. The motor torque, $\tau_M(t)$ causes movement of the screw 332 (or any other suitable linear actuator) in a direction along the longitudinal axis 122.

1.3 System Diagram

Figure 3:
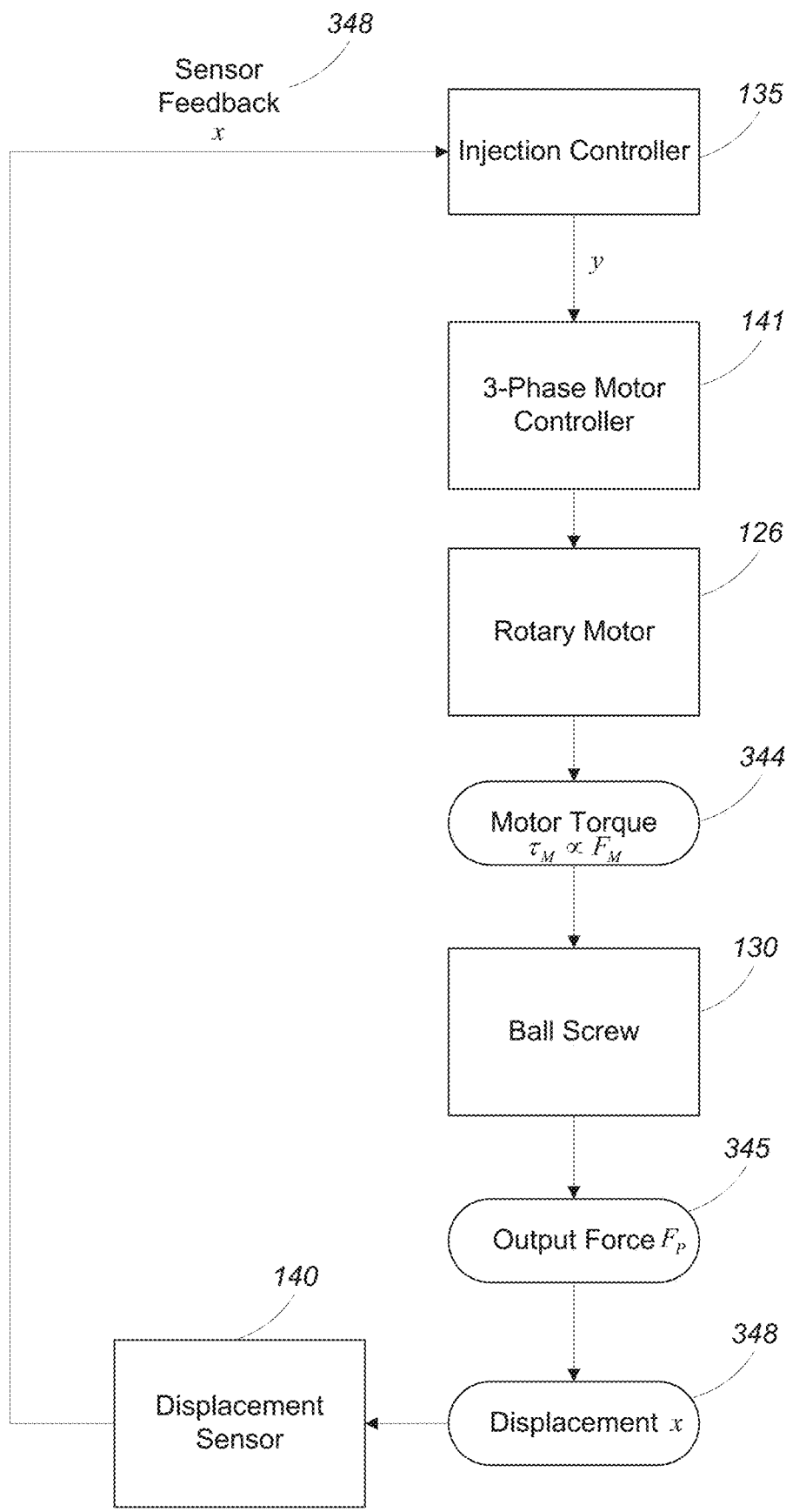
FIG. 3 is a block diagram of the controllable, needle-free transdermal injection device of FIG. 1.

Referring to FIG. 3, a schematic diagram of the system of FIG. 1 shows the rotary motor torque $\tau_M$ being applied to the ball screw 130 in step 344. Application of the rotary motor torque, at a given time $t_1$ by the rotary motor causes application of a force, $F_M(t_1)$ to the screw 332 of the ball screw 130 as shown in step 345, which in turn causes a displacement of the screw 332 in step 348.

The displacement of the screw 332 of the ball screw 130 is measured by the displacement sensor 140 and is fed back to the injection controller 135. As is described in greater detail below, the injection controller 135 processes the measured displacement to provide sensor feedback 348 to determine a motor control signal $y(t_1)$ which is supplied to the three-phase motor controller 141. The three-phase motor controller 141 drives the rotary motor 326 according to the motor control signal $y(t_1)$, causing the motor 126 to apply a torque $\tau_M(t_2)$ to the screw 332 of the ball screw 130 at a time $t_2$. As is noted above, the torque $\tau_M$ applied to the screw 332 causes application of a force $F_P$ to the plunger 120 with $F_P$ being determined as:

$$F_P = \frac{\tau_M 2\pi\eta}{P}$$

where $F_P$ is a force applied to the plunger 120 by the screw 332, $\tau_M$ is a torque applied to the screw 332, $\eta$ is an efficiency of the ball screw actuator 130, and P is a lead of the screw 332.

Figure 4:
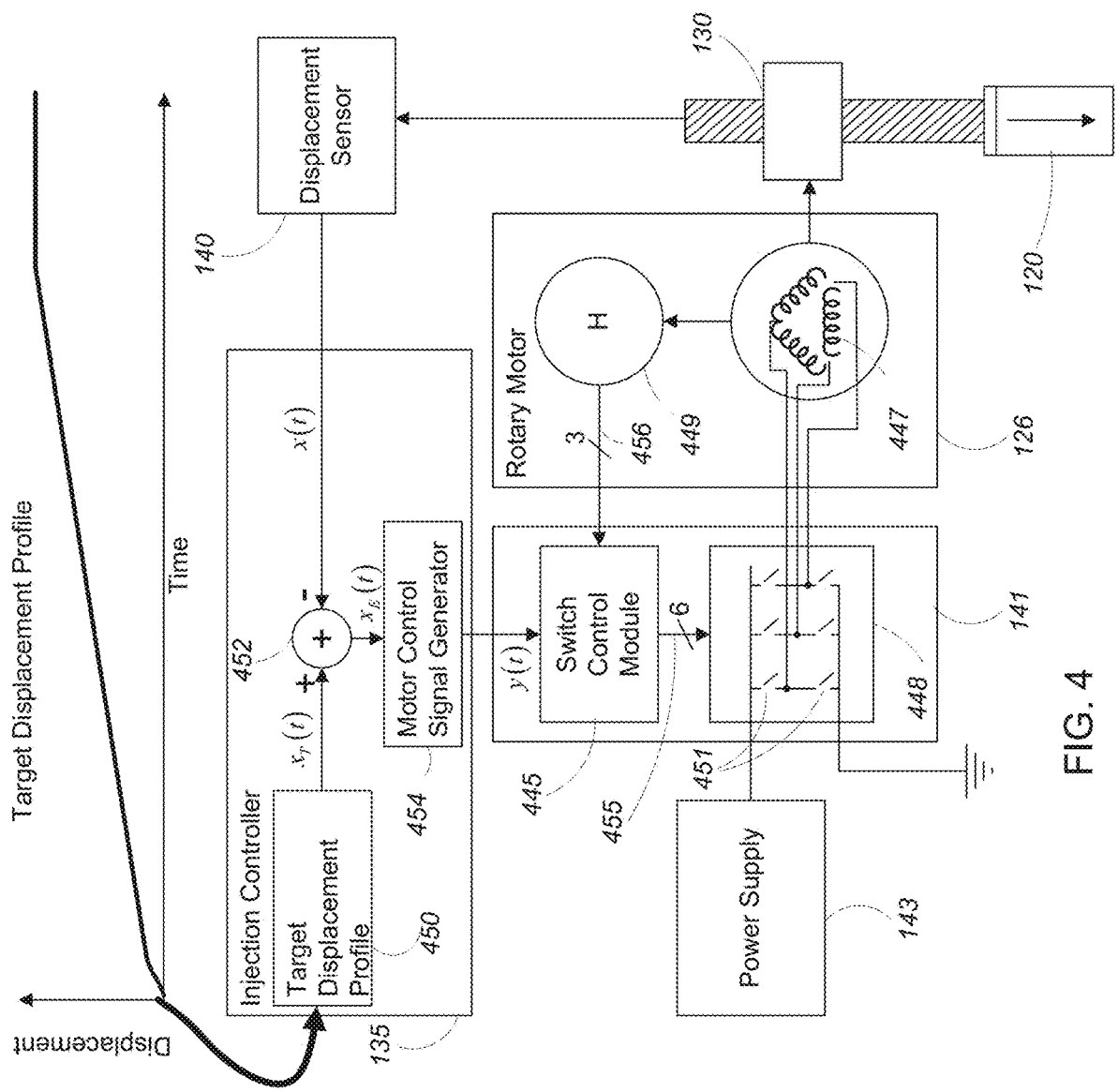
FIG. 4 is a detailed block diagram of the controllable, needle-free transdermal injection device of FIG. 1.

Referring to FIG. 4, in some examples the injection controller 135 includes a target displacement profile 450, a summing block 452, and a motor control signal generator 454. Very generally, the injection controller 135 receives a displacement value x(t) at time t from the displacement sensor 140. The time t is provided to the target displacement profile 450, which determines a target displacement value $x_T(t)$ for the time t.

In some examples, the target displacement profile 450 includes a mapping between target displacement values and times associated with an injection cycle (i.e., a range of time over which the plunger 120 of the device moves). For example, in the target displacement profile 450 shown in FIG. 4 the displacement starts at zero at the beginning of an injection cycle (i.e., at time $t_0$) and changes (e.g., increases) over time as the injection cycle proceeds, with each instant in time of the injection cycle being associated with a corresponding displacement value. As is described in greater detail below, in some examples the rate of change of the displacement values varies over time, with different time intervals of the injection cycle being associated with different rates of change of displacement values. Control of the plunger displacement, e.g., according to the target displacement profile 450, can be used to perform complex injections. For example, in one aspect, the plunger 120 is displaced relatively quickly during an initial piercing phase to penetrate the skin barrier, and in other time intervals the plunger 120 is displaced relatively slowly to deliver the injectate through an opening formed during the initial, piercing phase. In another aspect, the target displacement profile 450 may control multiple, sequential injections each having a biphasic profile with a piercing phase and a drug delivery phase. In practice, the actual displacement profile of the plunger 120 may vary from the ideal target displacement profile according to physical limits of the system and other constraints.

Both the measured displacement value x(t) and the target displacement value $x_T(t)$ are provided to the summing block 452. The summing block 452 subtracts the measured displacement value x(t) from the target displacement value $x_T(t)$ to obtain an error signal $x_E(t)$. The error signal $x_E(t)$ is provided to the motor control signal generator 454 which converts the error signal to a motor control signal y(t). The motor control signal y(t) is provided to the three-phase motor controller 141 or other suitable drive system, which in turn drives the motor 126 according to the motor control signal y(t).

In some examples, the rotary motor 126 may be a three-phase motor with three windings 447 and three Hall sensors 449, each Hall sensor 449 corresponding to a different one of the three windings 447. Each of the windings 447 is wrapped around a laminated soft iron magnetic core (not shown) so as to form magnetic poles when energized with current. Each of the three Hall sensors 449 generates a corresponding output signal 456 in response to presence (or lack of) a magnetic field in its corresponding winding 447.

The three-phase motor controller 141 includes a switch control module 445 and a switching module 448. The switching module 448 includes three pairs of switches 451 (with six switches 451 in total), each pair of switches corresponding to a different one of the windings 447 of the rotary motor 126 and configurable to place the corresponding winding 447 into electrical connection with the power supply 143 (whereby the winding is energized) or with ground. The switch control module 445 receives the motor control signal y(t) from the injection controller 135 and the three Hall sensor output signals 456 as inputs and processes the inputs to generate six switch control signals 455, each switch control signal 455 configured to either open or close a corresponding switch 451 of the switching module 448.

The above-described configuration implements a feedback control approach to ensure that a combination of the controlled torque applied to the screw 332 of the ball screw 130 due to the motor 126 causes the displacement of the plunger to track the target displacement profile 450 as the screw 332 is displaced.

1.4 Power Supply

Figure 5:
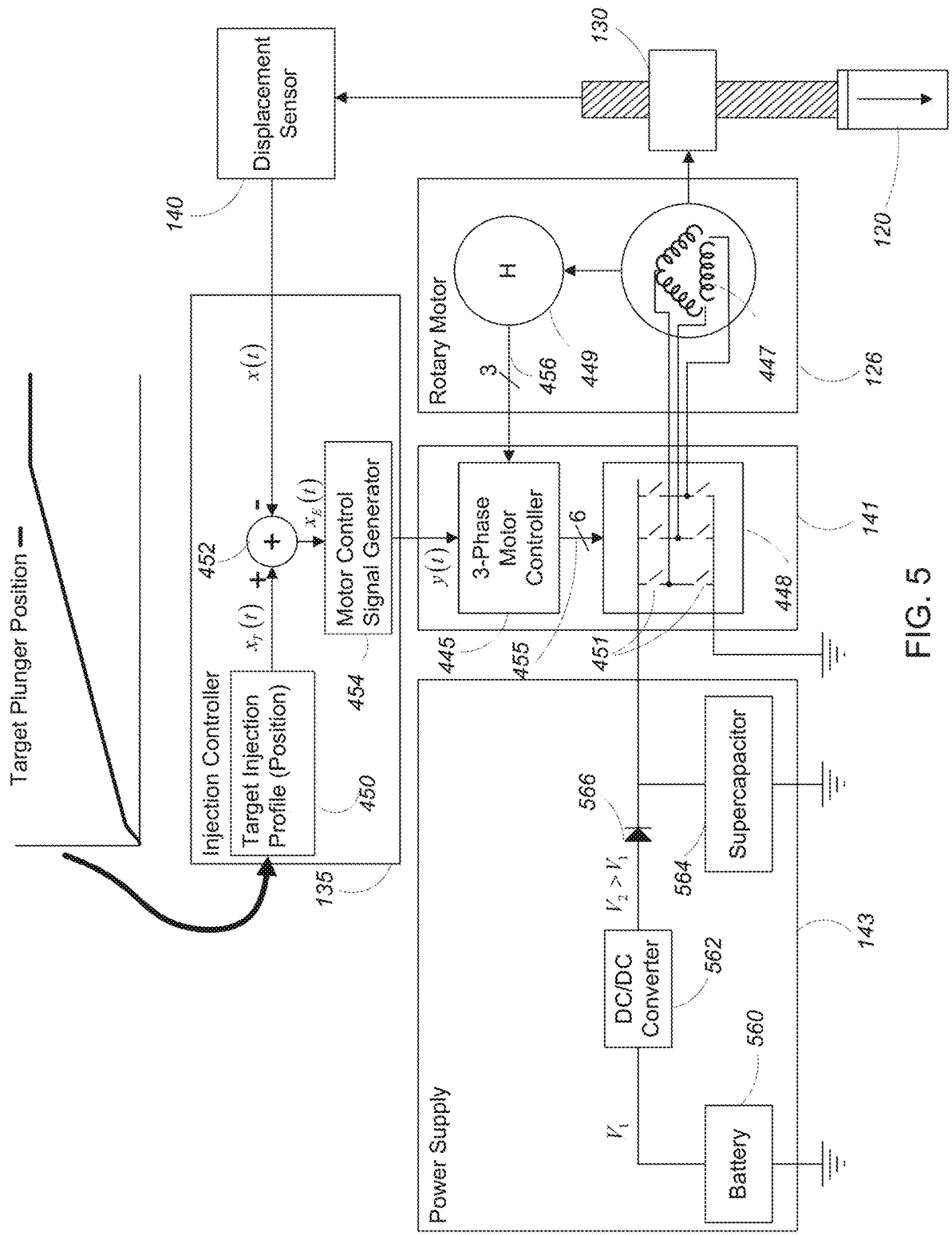
FIG. 5 is a detailed block diagram of the power supply of the controllable, needle-free transdermal injection device of FIG. 1.

Referring to FIG. 5, in some examples, the power supply includes a battery 560 (e.g., a Nickel Cadmium battery, a Nickel-Metal Hydride battery, a Lithium ion battery, an alkaline battery, or any other suitable battery type) configured to supply a voltage $V_1$ to a DC/DC converter 562 (e.g., a boost converter). The DC/DC converter 562 receives the supply voltage $V_1$ from the battery 560 as input and generates an output voltage $V_2$ greater than $V_1$. In some examples, the DC/DC converter 562 is configured to boost the supply voltage by a factor in the range of 5 to 20. While the battery 560 may be rechargeable, the battery 560 may also usefully store sufficient energy for multiple injections, such as two or more one milliliter injections, e.g., from replaceable single-dose cartridges or from a single, multi-dose cartridge.

The output voltage $V_2$ may be provided in parallel to a supercapacitor 564 and to the switching module 448 of the three-phase motor controller 141 via a diode 566. In operation, the output voltage $V_2$ charges the supercapacitor 564 while the transdermal injection device 100 is inactive. When an injection operation commences, the switches 451 of the switching module 448 close (according to the switch control signals 455), connecting the windings 447 of the rotary motor 126 to the supercapacitor 564. This results in a discharge of the supercapacitor 564, causing current to flow through the windings 447 of the rotary motor 126 and induce rotation of the rotary motor 126.

In some examples, the supercapacitor 564 includes a number of supercapacitors coupled together with a switching network. When the transdermal injection device 100 is inactive, the switching network may be configured so that the number of supercapacitors is connected in parallel for charging. When an injection is initiated, the switching network may be reconfigured so that the number of supercapacitors are serially connected for discharge. In some examples, the supercapacitor 564 is configured to deliver a peak power of 200 Watts or more to the ball screw 130 via the rotary motor 126.

In general, the supercapacitor may be any high-capacity capacitor suitable for accepting and delivering charge more quickly than a battery or other source of electrical energy. A wide variety of supercapacitor designs are known in the art and may be adapted for use as the supercapacitor 564 contemplated herein, such as double-layer capacitors, pseudocapacitors, and hybrid capacitors. Similarly, the supercapacitor 564 may usefully include any number and arrangement of supercapacitors suitable for delivering electrical power in an amount and at a rate suitable for driving a rotary motor 126 of an injection device 100 as contemplated herein.

2 Target Displacement Profile

Referring to FIG. 6, one example of a target displacement profile includes a number of injection phases, each associated with a corresponding time interval.

A first injection phase 670 is associated with a first time interval extending from time $t_0$ to time $t_1$. In the first injection phase 670, the target displacement of the plunger 120 is at a constant initial position $p_0$ where the plunger 120 is engaged with the injectate in the chamber 106. In this phase, the injection device 100 is generally prepared to perform an injection operation. In general, the first injection phase 670 may be preceded by any number of preparatory steps or phases, such as loading of an injectate (or a cartridge containing an injected) into the injection device, the removal of bubbles from the injectate as necessary or appropriate, measuring environmental conditions, measuring parameters of an injection site, and any other steps or combination of steps useful for performing, or preparing to perform, a needle-free injection as contemplated herein.

In one aspect, the rotary motor 126 may be mechanically engaged with the ball screw actuator 130 (or any other suitable linear actuator) while the rotary motor 126 is stationary in the first injection phase 670. That is, the rotary motor 126 may be pre-engaged with the ball screw actuator 130 and preload to remove any mechanical slack in the mechanical components of the system. In this configuration, a mechanical switch or the like may be used to prevent relative movement of the components, and/or a gate or seal may be used at the nozzle exit to prevent leakage of drug from the chamber 106. In another aspect, the rotary motor 126 may be slightly spaced apart from engagement with the ball screw actuator 130. In this latter configuration, the rotary motor 126 may usefully accelerate (while unloaded) into engagement with the ball screw actuator 130 at an end of the first injection phase 670 or at a beginning of the second injection phase 672 to facilitate a greater initial velocity of injectate from the nozzle. This may, for example, include a single rotation of the rotary motor 126 from engagement with the ball screw actuator 130, or a fractional rotation suitable to facilitate very high initial rotational acceleration.

A second injection phase 672 is associated with a second time interval extending from time $t_1$ to $t_2$. In the second injection phase 672, movement of the plunger 120 may be initiated. In this phase, the target displacement of the plunger 120 increases at a relatively high first rate to move the plunger 120 from the initial position $p_0$ to a first position $p_1$. In general, the motion of the plunger 120 in this phase may cause a jet of injectate to be ejected from the chamber 106 of the injector head 104 (via the opening 114) with a first velocity $V_1$ at least sufficient to pierce human tissue to a subcutaneous depth. In some examples, the second injection phase 672 spans a time interval less than 100 ms (i.e., the difference between $t_1$ and $t_2$ is less than 100 ms). In some examples, the second injection phase 672 spans a time interval less than 60 ms (i.e., the difference between $t_1$ and $t_2$ is less than 60 ms). In some examples, the second injection phase 672 spans a time interval less than 10 ms (i.e., the difference between $t_1$ and $t_2$ is less than 10 ms).

More generally, the injection device 100 may be configured so that in this second injection phase 672, the plunger 670 transitions from a stationary position to the target velocity at a sufficient rate for the initial stream of injectate to achieve a piercing velocity substantially instantaneously, e.g., without substantial leakage or loss of injectate at the surface. By configuring the linear drive system described above to accelerate in this manner from a fixed position to a piercing velocity, the injection device 100 may advantageously mitigate loss of injectate. As a further advantage, an injection device with this capability can usefully perform multiple sequential injections without requiring any physical recharge or resetting of a mechanical stored energy system.

A third injection phase 674 is associated with a third time interval extending from time $t_2$ to $t_3$. In the third injection phase 674 the target displacement of the plunger increases at a rate substantially the same as the first rate to move the plunger 120 from the first position $p_1$ to the second position $p_2$. In this third injection phase 674, the plunger 120 may be moved at a rate to cause the jet of injectate to be ejected from the chamber 106 of the injector head 104 with a second velocity $V_2$ greater than or equal to the first velocity $V_1$. While the rate of plunger 120 movement and the velocity of the injectate stream may vary within this third injection phase 674, e.g., according to limitations on control precision, physical system components, and so forth, the plunger 120 should generally be driven at a minimum velocity suitable for piercing tissue at a target site to a desired depth for delivery of the injectate. The jet of injectate may also have a maximum velocity selected to avoid over-penetration or other undesirable tissue damage.

A fourth injection phase 676 is associated with a fourth time interval extending from time $t_3$ to time $t_4$. In the fourth injection phase 676 the target displacement of the plunger 120 increases at a third rate, relatively slower than the first rate, to move the plunger 120 from the third position $p_3$ to a fourth position $p_4$. In this fourth injection 676, the injection device 100 may generally decelerate the plunger 120 to cause the jet of injectate to eject from the chamber 106 of the injector head 104 with a third velocity $V_3$ less than the first velocity $V_1$, which may generally be any velocity suitable for non-piercing delivery of additional injectate at a current depth of the stream of injectate within the target tissue.

A fifth injection phase 678 is associated with a fifth time interval extending from time $t_4$ to $t_5$. In the fifth injection phase 678 the target displacement of the plunger 120 continues to increase at the third rate to move the plunger 120 from the fourth position $p_4$ to the fifth position $p_5$. In the fifth injection phase 678, the injection device 100 may generally deliver the injectate—typically a majority of the injectate in the chamber 106—at a subcutaneous depth achieved during the prior, piercing phase. The rate of movement may be generally constant, or may otherwise vary consistent with maintaining subcutaneous drug delivery without further piercing of the tissue.

It will be appreciated that some continued piercing may occur during the fifth injection phase 678. Provided that any additional piercing does not create a pathway below subcutaneous depth within the target tissue that might result in loss or misdelivery of therapeutic dosage, then this additional piercing will not affect the efficacy of transdermal drug delivery. It will also be understood that the total displacement of the plunger 120 will control the volume of drug delivered over the course of an injection, and a duration of the fifth injection phase 678 may correspondingly be selected according to an intended dosage.

Finally, a sixth injection phase occurs after time $t_5$. In the sixth injection phase the target displacement of the plunger 120 stops increasing, substantially halting the plunger 120 at a sixth position $p_6$. The sixth injection phase is associated with completion of the injection operation. As noted above, from this position, additional injection cycles may be initiated, provided of course that sufficient additional drug remains in the injection device 100 for completing additional injections.

In order to quickly achieve a piercing velocity and avoid loss of drug at the surface of an injection site, the second injection phase 672 (where acceleration of the injectate occurs) may be short relative to the piercing phase that is maintained once the piercing velocity is achieved. Thus in some examples, the time interval associated with the third injection phase 674 is in a range of two to twenty times as long as the time interval associated with the second injection phase 672. In some examples, the time interval associated with the second injection phase 672 has a duration between 30 milliseconds and 100 milliseconds and the time interval associated with the third injection phase 674 has a duration between 100 milliseconds and 1000 milliseconds.

More generally, the duration of each phase may depend on the diameter of the injectate stream, the properties of the injectate, the characteristics of the tissue at the injection site and so forth. Thus, the injection profile may usefully employ any durations suitable for accelerating to a piercing velocity sufficiently rapidly to avoid substantial loss of injectate, maintaining a piercing velocity until a target depth (e.g., subcutaneous depth) is achieved, and then maintaining a non-piercing velocity to deliver a full dose at the target depth.

It will also be understood that, while a single injection cycle is illustrated, the injection device 100 contemplated herein may usefully be configured for multiple, sequential injections. As such any number of injection cycles might usefully be performed, and any such multi-injection applications are expressly contemplated by this description.

2.1 Rotary Motor Speed

Referring to FIG. 7, in the first injection phase 670, the injection controller 135 controls the rotary motor 126 to maintain its speed at substantially 0 rotations per minute (RPM) to ensure that the plunger 120 remains stationary at the initial position $p_0$. This may include actively maintaining the rotary motor 126 in a fixed position, e.g., by monitoring the position and activation the rotary motor 126 in counter-response to any detected motion or drift, or by control a magnetic, mechanical, or electromechanical lock that securely engages the plunger 120 in the initial position $p_0$. In another aspect, this may include passively maintaining the rotary motor 126 in the fixed position by withholding control signals or drive signals from the rotary motor 126. It will also be understood that combinations of the foregoing may advantageously be employed. For example, the plunger 120 may be locked with a mechanical lock during storage or while otherwise not in use, and then the rotary motor 126 may be used to electromechanically and actively lock the position of the plunger 120 when the mechanical lock is disengaged to prepare for an injection. In this manner, power may be conserved during long term storage, while the position can be securely and controllably locked using the rotary motor 126 in an interval immediately prior to injection in order to prevent, e.g., leakage of an injectate.

In the second injection phase 672, the injection controller 135 may control the rotary motor to accelerate from 0 RPM to a first rotary motor speed $S_1$ (e.g., 33,000 RPM), causing the plunger 120 to move from the initial position $p_0$ to the first position $p_1$. In the third injection phase 674, the injection controller 135 may control the rotary motor 126 to maintain a speed at or above the first rotary motor speed $S_1$, causing the plunger 120 to move from the first position $p_1$ to the second position $p_2$. In the fourth injection phase 676, the injection controller 135 may control the rotary motor 126 to decelerate to a second rotary motor speed $S_2$ (e.g., 11,000 RPM) less than the first rotary motor speed $S_1$, causing the plunger 120 to move from the second position $p_2$ to a third position $p_3$. In the fifth injection phase 678, the injection controller 135 may control the rotary motor 126 to maintain the second rotary motor speed $S_2$, causing the plunger 120 to move from the third position $p_3$ to a fourth position $p_4$ at a substantially consistent rate for delivery of an injectate at a target depth for an injection.

In the sixth injection phase, the injection controller 135 may control the rotary motor 126 to decelerate its speed from the second rotary motor speed $S_2$ to 0 RPM, causing movement of the plunger 120 to substantially halt at the fourth position $p_4$.

While the supercapacitor 564 in the power supply 143 described above may be used during any portion of the injection delivery, the supercapacitor 564 may be particularly advantageous where high mechanical loads are anticipated, e.g., during the initial acceleration and piercing phases, as well as where necessary or helpful to quickly decelerate or stop the plunger 120, e.g., at the fourth position $p_4$. Thus, the supercapacitor 564 may be specifically used during the second injection phase 672, the third injection phase 674, and optionally the fourth injection phase 676 if high power is required to maintain a target speed even during a deceleration of the injectate to a drug delivery velocity, and/or if high power is required to quickly decelerate or stop the plunger 120.

2.2 Injectate Velocity

Figure 8:
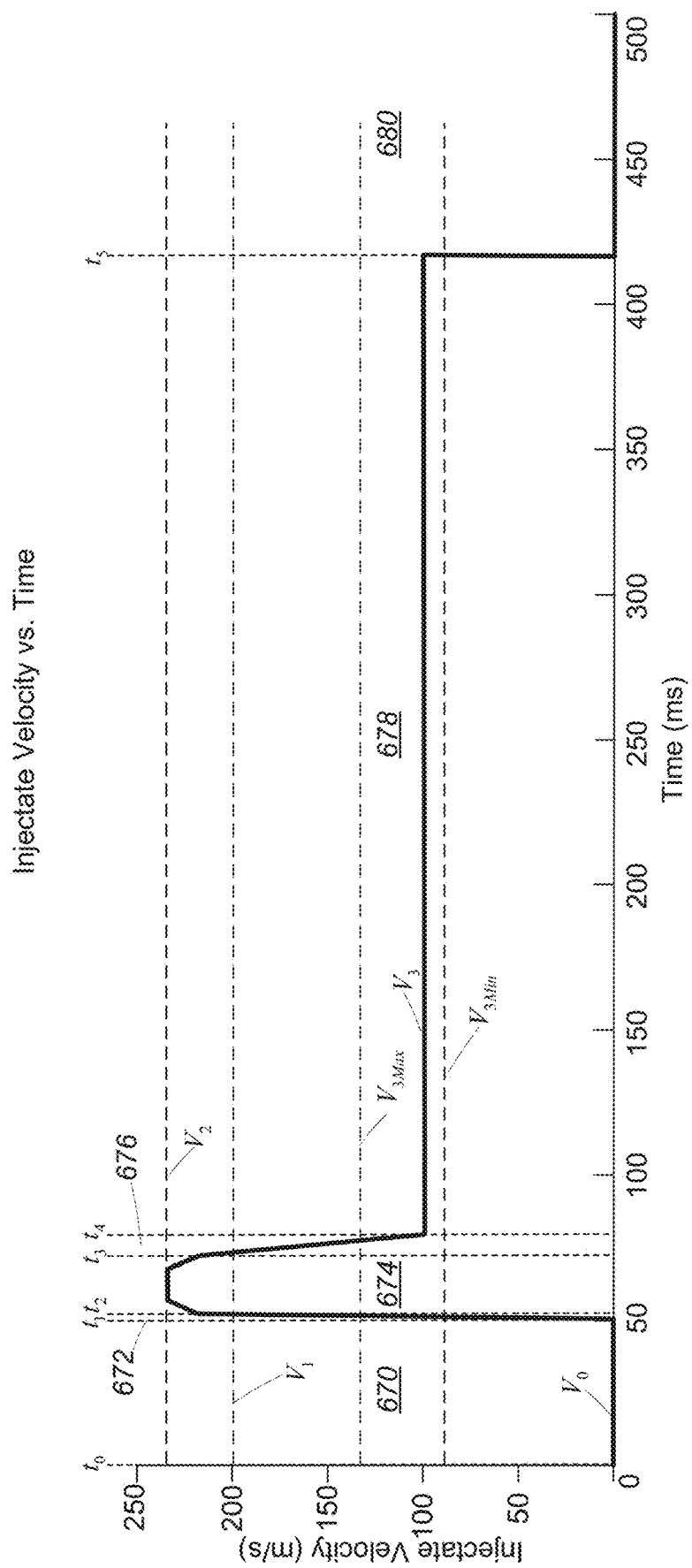
FIG. 8 is an injectate jet velocity profile associated with the target displacement profile of FIG. 6.

Referring to FIG. 8, in the first injection phase 670, no injectate is ejected from the chamber 106 (i.e., the initial injectate velocity, $V_0$ is 0 m/s). In the second injection phase 672, the injectate velocity increases from 0 m/s to the first velocity, $V_1$ at least sufficient to pierce human tissue. In some examples, the first velocity $V_1$ is at least 200 m/s. If piercing is not initiated quickly, then there may be substantial loss or leakage of drug. Thus, in some embodiments, the rotary motor 126 may usefully be configured to reach the first velocity $V_1$ for injection from a stationary starting point in not more than three rotations, such as less than two rotations, or less than one rotation.

In the third injection phase 674, the injectate velocity may be maintained at a second velocity $V_2$ greater than or equal to the first velocity $V_1$ in order to continue piercing tissue at a target site. Where the first velocity $V_1$ is a minimum velocity for piercing tissue, then the second velocity $V_2$ is preferably maintained above the first velocity $V_1$ in order to continue piercing throughout the third injection phase 674. However, the first velocity $V_1$ may instead be a minimum velocity or an optimum velocity to initiate piercing, in which case the second velocity $V_2$ may usefully be any velocity greater than, equal to, or less than the first velocity $V_1$ suitable for continuing to pierce tissue to the desired, target depth. Similarly, the second velocity $V_2$ may vary over the duration of the third injection phase 674 provided that the second velocity $V_2$ remains within this window of useful piercing velocities.

In the fourth injection phase 676, the injectate velocity may decreases to a third velocity $V_3$ (in a range between a maximum third velocity $V_{3Max}$ and a minimum third velocity $V_{3Min}$) sufficient to deliver the majority of the injectate in the chamber 106 at a subcutaneous depth. In the fifth injection phase 678, the injectate velocity may be substantially maintained at the third velocity $V_3$ while the majority of the injectate in the chamber 106 is delivered to the subcutaneous depth through the channel created during the third injection phase 674. It will be appreciated that the third velocity $V_3$ may vary over the course of the fifth injection phase 678 between any values—typically greater than zero and less than a piercing velocity—consistent with delivery of the injectate at the target depth. Finally, in the sixth injection phase 680, the injectate velocity may decrease to 0 m/s as the injection operation completes.

3 Injectate

In some examples, the volume of injectate in the chamber is at least one milliliter. Thus, in one aspect the injection device 100 may be configured to deliver one milliliter of drug subcutaneously in a single dose, or as a number of sequential doses over time, e.g., to different locations or over the course of an extended dosing schedule. Where a large number of sequential doses are intended, or where a larger single dose is intended (e.g., more than one milliliter) the chamber may usefully have a greater volume. For multi-dose applications, the contents of the chamber 106 may be conveniently distributed in discrete doses using a rotary motor and linear drive system as contemplated herein. In some examples, the volume of injectate in the chamber is less than or equal to approximately 0.5 milliliters. In some examples, the volume of injectate in the chamber is less than or equal to approximately 0.3 milliliters. In some examples, the volume of injectate in the chamber is a therapeutic amount of injectate.

In some examples, the injectate includes a biological drug. In some examples, the injectate has a viscosity of at least three centipoise at a temperature between two degrees and twenty degrees Celsius. In some examples, the injectate has a viscosity of about three centipoise to about two hundred centipoise at a temperature between two degrees and twenty degrees Celsius. Thus, the system described herein may usefully be employed with large molecule therapeutics or other drugs having relatively high viscosities.

4 Miscellaneous

In one aspect, the injection controller may be configured to cause the needle-free transdermal injection device 100 to perform a number of sequential injection operations in close temporal proximity to one another. The injection device 100 may usefully be instrumented to support this operation by sensing movement of the injection device 100 and providing tactile, visible, audible or other feedback to aid in navigating the user through a multi-injection procedure.

In another aspect, a number of sequential injection operations may be performed without having to reverse the movement of the rotary motor (i.e., to withdraw the plunger). Thus, where additional injectate remains in the injection device 100 at the end of an injection cycle sufficient for an additional dose, the rotary motor 126 may remain stationary, and a second, complete injection cycle may be initiated from this new starting position. In this context, the rotary motor 126 may be manually locked, or electromagnetically maintained in a fixed location in order to prevent leakage or other loss of therapeutic product.

In some examples, the linkage (e.g., the ball screw linkage) is bidirectionally coupled to the rotary motor and the plunger such that bidirectional displacement of contents in the chamber is possible, e.g. by moving the plunger toward an exit nozzle to eject contents, or moving the plunger away from the exit nozzle to load additional drug into the injection device 100.

In some examples, the transdermal injection device includes a sensor system for detecting when the device is properly positioned for performing an injection operation. In some examples, once the device is properly positioned, the injection controller is configured to initiate the injection operation without any observable latency. That is, the sensor system may monitor the injection device 100, determine when the injection device 100 is properly positioned and stationary, and then initiate an injection. Depending on the duration and feel of the injection, the injection may usefully be preceded by a beep, vibration, or other human-perceptible signal alerting a user that the injection is about to occur.

In some examples, one or more conventional capacitors (e.g., electrolytic capacitors) can be used instead of or in addition to the supercapacitor.

In some examples the injection controller is configured to prevent two or more injection operations within a predetermined minimum injection cycle time. Thus, for example, where a dosing regimen specifies a minimum time before injections, or where an injection is being delivered as a sequence of injections in different but adjacent locations, the injection controller may monitor activation of the injection device 100 to ensure that any rules for a corresponding injection protocol are adhered to.

In some examples, the needle-free transdermal injector head is formed as a removable cartridge for containing injectate. The removable cartridge has an opening with a predetermined shape for ejecting the injectate in a stream with a predetermined shape. In some examples, the needle-free transdermal injector includes a movable cartridge door mechanism. A user can interact with the movable cartridge door mechanism to load cartridges into the needle-free transdermal injector and to unload cartridges from the needle-free transdermal injector.

While the above description relates primarily to methods and apparatuses for the injection of therapeutics through human tissue to a subcutaneous depth, it is noted that, in some examples the methods and apparatuses described above are used for injection of therapeutics through human tissue to other shallower or deeper depths. For example, the methods and apparatuses can be used for a shallow injection of therapeutics into the dermis, or for a deeper injection though the subcutaneous layer of fat and connective tissue into a patient's musculature.

In one aspect, an injector as contemplated herein may be improved by monitoring the compression of a gas bubble within a cartridge of injectate during operating of a plunger in a pre-injection phase. Where a cartridge of liquid injectate such as a therapeutic includes a gas bubble, either as a regulatory requirement or a manufacturing artifact, this can make it more difficult to accurately control an injection by introducing a compressible region into an otherwise generally incompressible volume of injectate. By decoupling a phase of an injection during which the gas bubble is highly compressible (e.g., while being compressed) from a phase of the injection where the gas bubble is relatively incompressible, an improved control system may be obtained. In general, when the gas bubble becomes sufficiently compressed (e.g., at or near the equilibrium pressure during the piercing phase), the velocity of the plunger of the needle-free injector is changed to the piercing rate for delivery of the injectate to a target. By detecting the gas bubble compression prior to delivery of injectate in this manner, an injection stream can be controlled to more closely reproduce a target injection profile. For example, the integrator error for an injector control model can be mitigated, stream acceleration can be optimized/maximized, and overshoot in the injector response (e.g., stream velocity or plunger movement) can be minimized.

In one aspect, an open or free running model is created that models behavior of the injector hardware without the load of an injectate. This model provides an estimate of free run characteristics including plunger speed and plunger position for a system that is operating to linearly move a plunger without ejecting a fluid for injection. The free run state is generally linear in nature, which facilitates an analytic solution that can be deployed on computing platform such as a micro-controller for a medical device.

A free run system model can be represented by the second order linear ordinary differential equation ("ODE"):

$$C_1\theta''(t)+C_2\theta'(t)=\tau \qquad \text{Equation 1}$$

Where:
$C_1$ is the total system inertia as seen by the actuator in $$\frac{kg}{m^2}$$

$C_2$ is the total system damping as seen by the actuator in $$\frac{Nms}{rads}$$

$\theta'(t)$ is the rotational velocity in $$\frac{rads}{s}$$

$\theta''(t)$ is the rotational acceleration in $$\frac{rads}{s^2}$$

$\tau$ is the torque applied by the motor.

$$\frac{N}{m}$$

The general solution of a second order nonhomogeneous linear equation is:

$$\theta=\theta_c+\theta_p \qquad \text{Equation 2}$$

Where $\theta_c$ is the complimentary solution and $\theta_p$ is the particular solution. To solve the ODE for the complimentary solution Equation 1 is set equal to zero and a general solution of the following form is assumed:

$$\theta(t)=e^{\lambda t}$$

$$\theta'(t)=\lambda e^{\lambda t}$$

$$\theta''(t)=\lambda^2 e^{\lambda t}$$

The Characteristic Polynomial is:

$$C_1\lambda^2 e^{\lambda t}+C_2\lambda e^{\lambda t}=0$$

$$C_1\lambda^2+C_2\lambda=0 \qquad \text{Equation 3}$$

Solving for the Characteristic Roots results in:

$$\lambda_{1,2} = \left(0, -\frac{c_2}{c_1}\right)$$

We have two distinct real roots for this solution, yielding two solutions:

$\theta_1(t)=1$ and $\theta_2(t)=e^{-C_2t/C_1}$

The Complimentary Solution is of the form:

$$\theta_c = k_1\theta_1 + k_2\theta_2 = k_1 + k_2 e^{-C_2t/C_1} \quad \text{Equation 4}$$

The Particular solution requires any function that satisfies the nonhomogeneous equation. For Equation 1, the form is determined using the method of unknown coefficients, where:

$\theta_p = At$ $\theta'_p = A$ $\theta''_p = 0$

Plugging this into Equation 1, $C_1 * 0 + C_2 * A = \tau$ and solving for the coefficient A:

$$A = \frac{\tau}{C_2}$$

resulting in a Particular Solution of:

$$\theta_p = \frac{\tau}{C_2} t \quad \text{Equation 5}$$

The general solution is obtained by plugging $\theta_c$ (as expressed in Equation 4) and $\theta_p$ (as expressed in Equation 5) into Equation 2:

$$\theta(t) = k_1 + k_2 e^{-C_2t/C_1} + \frac{\tau}{C_2} t \quad \text{Equation 6}$$

A solution for the constants $k_1$ and $k_2$ can be found by assuming initial conditions:

$\theta(0)=\theta_0$ and $\theta'(0)=\theta'_0$

This results in a set of equations from Equation 6:

$$\theta(0) = \theta_0 = k_1 + k_2$$

$$\theta'(0) = \theta'_0 = -\frac{c_2}{c_1}k_2 + \frac{\tau}{C_2}$$

Solving for $k_1$ and $k_2$:

$$k_2 = \frac{C_1}{C_2}\left(\frac{\tau}{C_2} - \theta'_0\right)$$

$$k_1 = \theta_0 - k_2 = \theta_0 - \frac{C_1}{C_2}\left(\frac{\tau}{C_2} - \theta'_0\right)$$

Finally, a solution can be obtained by substituting $k_1$ and $k_2$ into Equation 6:

$$\theta = \theta_0 - \frac{C_1}{C_2}\left(\frac{\tau}{C_2} - \theta'_0\right) + \frac{C_1}{C_2}\left(\frac{\tau}{C_2} - \theta'_0\right)e^{-C_2t/C_1} + \frac{\tau}{C_2}t \quad \text{Equation 7}$$

This solution can be used to estimate the free run plunger position of an injection device given an initial position $\theta_0$, initial rotational velocity $\theta'_0$, a motor torque $\tau$, and a time step t. Taking a time derivative of the position in Equation 7 results in an equation for velocity:

$$\theta' = \left(\theta'_0 \frac{\tau}{C_2}\right)e^{-C_2t/C_1} + \frac{\tau}{C_2} \quad \text{Equation 8}$$

The system inertia $C_1$ is derived from the physical system. In order for the model to accurately simulate the physical system, loads due to inertia need to be considered. Inertia is imparted by all moving parts of the actuator assembly, including:

Motor ($I_m$): The inertia of the internal moving parts of the Maxon ECX 16. This value is given on the motor data sheet. For the ECX 16, the data sheet specifies the Rotor Inertia as 1.2 g·cm$^2$ or 1.2e−7 kg·m$^2$ Gear 1 ($I_{G1}$): This is the first gear attached to the motor output shaft. Inertia may be determined by Solidworks or any other suitable modeling environment given gear dimensions and materials. This was calculated using Solidworks to be 8.9e−10 kg·m$^2$ Gear 2 ($I_{G2}$): This is the second gear attached to the motor output shaft. Inertia was determined by Solidworks given gear dimensions and materials. Its rotation rate is different from that of the motor shaft and thus the reflected inertia through the drive chain will be calculated. Inertia was calculated to be 5.862e−7 kg·m$^2$ before the transformation through the drive train.

$$I_{G2\_m} = \left(\frac{1}{GR}\right)^2 I_{G2} = \left(\frac{1}{5.6}\right)^2 5.862e-7 = 1.869e-8 \text{ kg·m}^2$$

Lead Screw ($I_{LS}$): For the lead screw we need to determine how the inertia of a linear moving mass impacts the rotational inertia of the motor.

$$I_{LS} = M\left(\frac{p}{2\pi}\right)^2 \frac{1}{e} = 20.245e-3 \text{ kg} \left(\frac{3e-3}{2\pi}\right)^2 \frac{1}{0.95} = 4.8582e-9 \text{ kg·m}^2$$

This inertia also acts through the gear train so we convert it similar to Gear 2.

$$I_{LS\_m} = \left(\frac{1}{GR}\right)^2 I_{LS} = \left(\frac{1}{5.6}\right)^2 4.8582e-9 = 1.5492e-10 \text{ kg·m}^2$$

The total rotational inertial load at the motor is obtained by summing the pieces above:

$C_1 = I_{total} = I_m + I_{G1} + I_{G2\_m} + I_{LS\_m} = 1.397\text{ed-7 kg·m}^2$ The damping constant for the system, $C_2$, was inferred by obtaining data from a physical device during an injection and selecting a value for $C_2$ that minimizes the model error.

For one physical instance of a needle-free injector driven by a rotary motor as generally described above, the calculated value was 15.0 e–7 (N·m·s)/rad.

Using the techniques described above, a model was created that provided an estimate of plunger velocity within 50 mm/s of the actual velocity, and converged to within 25 mm/s of the actual (measured) velocity during steady state free run while the injector was in a bubble compression phase. It will be understood that the actual error may vary from device to device, and may depend on other context such as the injection velocity, fluid viscosity, temperature, and so forth. It will be understood that other techniques for estimating a free running or unloaded plunger velocity may also or instead be employed, and any technique that provides an estimate suitable for use in a control system as contemplated herein may also or instead be used to provide a velocity estimate without departing from the scope of this disclosure. It will also be noted that certain other physical characteristics such as deformation of a plastic cartridge containing an injectate may be accounted for. While a satisfactory model was created without accounting for this and other physical properties of the system, these aspects may also be modeled, e.g., using a lookup table, calibration, additional modeling, or some combination of these. It has been observed that the physical response can lag the model response when not accounting for these other physical aspects, particularly during periods of significant change (e.g., during high acceleration). This can result in greater than expected measurement error under certain conditions, particularly at those times when bubble compression is expected to occur. In order to account for this, a larger threshold may be used to evaluate the error between estimated and actual velocity, either at all times, or at times of large change in the estimated velocity, in order to mitigate false detection of bubble compression.

In general, during an injection, the model—an estimate of free running plunger velocity in response to a control input such as a motor controller output—may be run concurrently with the collection of real-time measurements from an injector. During a bubble compression phase, the model should generally match the measured behavior. However, when the bubble approaches full compression, the loaded operation of the plunger, which is then driving injectate from the cartridge, will deviate significantly from the free running model. This error can be used to detect effectively complete compression of the bubble of gas, at which time the controller may change from a bubble compression speed to a fluid ejection speed that is intended to drive the injectate from the injector according to an injection profile.

It should be appreciated that "full compression" or "effectively complete compression" in this context may refer to a variety of physical states. In general the compressibility of a gas such as air (or any other inert, sterile, or other gas contained in a cartridge along with an injectate) will vary with compression or pressurization. Thus the state of "full compression" as used herein need not refer to a particular physical degree of compression, and may instead generally refers to a state at which the remaining injection can be controlled as an incompressible or substantially incompressible fluid, e.g., without the presence of a compressible gas, to achieve a desired injection velocity profile. As a practical matter, this state of full compression may refer to a compression of the gas substantially equal to an amount of compression during steady state injection operation, or this may refer to a compression at which compressibility has fallen below a predetermined threshold, or a compression of the gas at which a meaningful error signal can be detected between physical operation and the free running model, or any other quantitative, physical, or other state of compression useful for controlling operation of the injector as contemplated herein.

Figure 9:
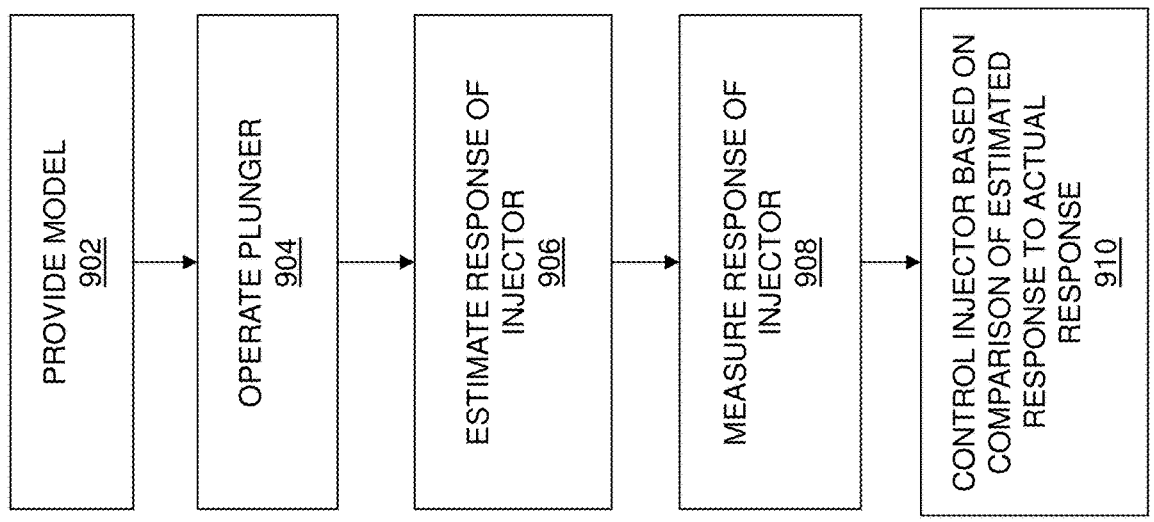
FIG. 9 shows a flow chart of a method for operating an injector.

FIG. 9 shows a flow chart of a method for operating an injector. More specifically, the method 900 may be used to operating a needle-free injector to issue a stream of injectate from a chamber containing the injectate and a gas bubble. In general, the model described above may be used to estimate a response of a plunger to a control signal, e.g., the velocity at which the plunger should be moving for a particular control or input signal. During operation, the actual velocity may also be measured and compared to the estimated velocity from the model. When the actual velocity deviates from the estimated velocity by a predetermined threshold, e.g., when the error exceeds some minimum amount, a controller for the injector may change from a bubble compression velocity selected to compress a gas bubble within a cartridge to an injection rate selected to eject fluid from the cartridge at a piercing velocity for a needle free injector.

The method 900 may begin with providing an injector such as any of the injectors described herein. This may include a needle-free injector having a controller, a cartridge containing an injectate and a gas bubble, a plunger, a nozzle or other injection orifice, and a drive system to drive the plunger in response to a control signal from the controller. The injector may also include any number of sensors or the like to control initiation of an injection and to monitor operation of the injector during operation.

As shown in step 902, the method 900 may include providing a model such as any of the models described above for characterizing free running response of the injector to a control input. For example, this may model a response of the needle-free injector to operation of a drive system for a plunger for the chamber without the injectate in the cartridge. As noted above, the model may include any suitable control model such as an analytical developed ODE model that relates an input such as a control signal or motor drive signal to an estimated rotational or linear velocity. The model may also be refined as described above to account for cartridge deformation, motor startup, or any other physical aspects of the system that may affect response to a control input. In general, the model may be stored in a memory of a controller for the injector in any manner suitable for real time execution and use during an injection.

In another aspect, the model may include a generalization based on the modeled free running-response or empirically observed behavior of the device. For example, the model may be simplified to provide a drive current threshold above which adequate gas compression is inferred. It will be noted that such a threshold will not generally apply during an initial acceleration of the plunger, e.g., when there is a current spike well before the compression in order to achieve a high rate of acceleration. Rather, the current threshold will apply during a stage when a steady velocity (either of the plunger, or a motor that drives the plunger) is being maintained. It will generally be expected that in a steady state, the drive current will similarly remain steady. However, as the system transitions from an unloaded state, e.g., when the uncompressed gas is compressing in response to advancement of the plunger but no fluid is being expelled from the injector, to a loaded or compressed state, the amount of drive current required to maintain a constant velocity will increase. While referred to herein as a spike above a threshold, it will be understood that for the purposes of this disclosure, the "spike" may include any increase in drive current to a level between the free-running level and the loaded level. As noted above, the free-running level used as a lower bound for this threshold may be a modeled or predicted current, a threshold level provided as a control parameter based on historical behavior, or a measured value captured during a current injection, e.g., after the initial current peak and associated acceleration. The upper bound for a loaded level will typically be about the current required to drive the motor while ejecting fluid during an injection. The threshold for transitioning from the compression state to the injection state may be any value between these upper and lower bounds, and may be a numerical value for drive current (or a corresponding control signal) or a ratio (e.g., relative to the actual steady state drive current observed once a steady state velocity is reached during the compression phase.

In general, the chamber may be a removable and replaceable cartridge for a needle-free injector, e.g., as described above. The injectate may include an injectable medication.

As shown in step 904, the method 900 may include operating the plunger of the injector. For example, this may include operating the plunger at a first rate with the drive system to move the plunger in a direction that displaces the injectate from the chamber through a nozzle. In general, the first rate may be different than the piercing rate, and may usefully be greater than the piercing rate. Operating at higher speed permits the greatest amount of compression of the bubble in a small interval before injectate begins exiting the injector as a coherent or collimated flow. In one aspect, the first rate may be a maximum rate achievable by the drive system, a rate substantially greater than the piercing rate, or some other rate greater than the piercing rate that facilitates rapid compression of a trapped gas bubble into a relatively incompressible state.

As shown in step 906, the method 900 may include estimating the response of the injector, e.g., by applying a control signal or other data indicative of an input to the injector to a model that estimates a response of the injector to the input. For an injector such as one of the needle-free injectors described herein this may include estimating the response of the needle-free injector with the model during operation of the drive system, thereby providing an estimated response. As noted above, the estimated response may more specifically be a free running or unloaded response, e.g. while moving a plunger without driving an injectate from the nozzle. The response may more specifically include a linear velocity (e.g., of a plunger), a rotational velocity (e.g., of a drive motor), or any other response that can be modeled on one hand and physically measured during operation of the injector on the other hand.

As shown in step 908, the method 900 may include measuring the response of the needle-free injector to the input. For example, this may include measuring the response with a sensor during operation of the drive system, thereby providing a measured response. This may include measuring any response suitable for comparison to the estimate provided by the model. This may include a direct comparison, e.g., where the model and the sensor both provide a linear velocity. This may also or instead include an indirect comparison, e.g., where the model provides a linear velocity, and the sensor provides a linear position, a rotational position, a rotational velocity, or any other metric that can be used to calculate or measure a property corresponding to the model output.

As shown in step 910, the method may include controlling the injector based on a comparison of the estimated response (from the model) to the actual response (from the sensor). In particular, this may include, while the measured response is within a predetermined threshold of the estimated response, inferring an uncompressed state of the gas bubble and maintaining operation of the plunger at about the first rate, and when the measured response exceeds the predetermined threshold from the estimated response, inferring a compressed state of the gas bubble and changing a velocity of the plunger to the piercing rate.

The first rate may, for example, be greater than the piercing rate, and/or may be a variable rate controlled within a predetermined range. In another aspect, this may include a maximum achievable rate for the plunger, or some other threshold larger than the piercing rate selected to transition to the piercing/injection stage as quickly as possible. In another aspect, the piercing rate may be a rate used to expel the injectate from the chamber at a velocity sufficient to pierce a skin of a patient receiving an injection from the needle-free injector.

The predetermined threshold of error for transitioning to the piercing phase may be any suitable threshold for detecting a physically meaningful deviation between the estimated and actual response of the injector including, e.g., an empirical threshold obtained by observing physical injections, an analytical threshold determined based on fluid dynamics, injector kinetics, gas compression, and so forth, or any other suitable threshold for controlling operation of the injector as described herein. Similarly, the gas bubble in the compressed state—for purposes of controlling operation of an injector as described herein—may be characterized in a number of ways. For example, the compressed state may be state at which the gas bubble is compressed to at least a pressure exerted on the chamber when operating the plunger at the piercing rate during the predetermined interval. Any other analytic proxy may also or instead be used for this compressed state. For example, the compressed state may be measured in terms of current compressibility of the gas state (e.g., has the bubble become effectively incompressible in the context of the remaining injection process), a change in volume of the bubble, an elasticity of the bubble's response to the plunger movement, or any other suitable measurement or proxy usefully for determining when to change from a bubble compressing stage of an injection to a fluid ejection stage of the injection. This may also or instead include a measure without clearly defined physical significance, provided the measure can be consistently applied to determine when a gas bubble has become sufficiently compressed to reduce or eliminate control errors or variability when switching to a piercing velocity.

In one aspect, the method 900 may further include, when the measured response exceeds the predetermined threshold, switching to a second model for loaded operation of the needle-free injector that includes injectate-cartridge interactions. At this point, the bubble has been effectively compressed, and the injector can be operated to generate a piercing stream of injectate from the nozzle of the cartridge or injector. This second phase of operation may be deterministically controlled, e.g., with open-loop control of the injector based on a deterministic control signal, and the second model may thus include an open-loop control model for a desired injection profile. In another aspect, this may include a controlled model, e.g., where position or some other parameter is measured and compared to a target parameter of an injection profile to provide a real time, controlled injection profile, e.g., throughout the entire injection cycle.

In another aspect, the method 900 may include implementing a biphasic injection profile, such as by, after a predetermined interval, decelerating the velocity of the plunger from the piercing rate to a drug delivery rate. As with the second model, this may include open loop control of the injection profile, feedback control of the injection profile, or some combination of these. Other injection profiles may also or instead be used, such as a slow steady decline in delivery rate over the course of fluid delivery, or a generally steady delivery rate, e.g., within a window and/or subject to control limits of the injector.

In another aspect, there is disclosed herein a method for performing a needle free injection from a chamber, the chamber having a plunger and an injection opening and the chamber containing an injectate and a gas bubble. The method may include initiating a first injection phase by operating a plunger for the chamber at a first velocity, monitoring a compression of the gas bubble during the first injection phase, when the gas bubble reaches a predetermined compression state, decelerating the plunger to a second velocity sufficient to drive the injectate through the opening at about a predetermined injectate velocity selected for piercing a target surface, operating the plunger at the second velocity for a first amount of time, and after the first amount of time, operating the plunger at a third velocity less than the second velocity until a predetermined volume of the injectate has been expelled from the chamber through the injection opening.

Operating the plunger at the first velocity may include operating the plunger at a maximum velocity, or operating the plunger at a maximum acceleration until a predetermined compression velocity is reached so that the gas bubble can be compressed as quickly as possible or practical before the injector begins displacing injectate from an orifice. Monitoring compression may, for example, include monitoring deviations from a control model as generally described above. Monitoring may also or instead include other techniques for monitoring compression, either directly or through a proxy such as plunger back force. In one aspect, monitoring the compression of the gas bubble may include monitoring a back force on the plunger. In another aspect, monitoring the compression of the gas bubble may include monitoring an injectate stream from the injector. In another aspect, monitoring the compression of the gas bubble may include estimating a compression time interval for the first injection phase to achieve the predetermined compression state of the gas bubble and operating at the first velocity for the compression time interval before switching to the second velocity. For example, this may include estimating the compression time interval by capturing an image of the gas bubble and estimating the volume of the gas bubble in order to calculate or otherwise estimate the compression time interval. In another aspect, video data may be acquired to graphically monitor the actual compression state and use this to determine when to change operation of the plunger to a piercing velocity.

In another aspect, an apparatus for injectate delivery as contemplated herein includes: a cartridge having a chamber containing a volume of an injectate and an exit port; a linear actuator coupled to a plunger and configured for delivery of the injectate from the exit port of the cartridge with the plunger, the linear actuator including a linkage; a rotary motor mechanically coupled to the linkage; a sensor for monitoring a pressure applied by the plunger to the cartridge; and a controller coupled to the rotary motor, the controller configured to control operation of the apparatus to perform the steps of: initiating a first injection phase by operating the plunger for the chamber at a first velocity; monitoring a compression of the gas bubble with the sensor during the first injection phase; when the gas bubble reaches a predetermined compression state, changing a velocity of the plunger to a second velocity selected to drive the injectate through the opening at about a predetermined injectate velocity; operating the plunger at the second velocity for a first amount of time; and after the first amount of time, operating the plunger at a third velocity less than the second velocity until a predetermined volume of the injectate has been expelled from the chamber through the injection opening.

The apparatus may be a needle-free injector. The sensor may include a force sensor. The sensor may also or instead include a pressure sensor for the chamber. The sensor may also or instead include a torque sensor for the rotary motor. In another aspect, the sensor may include an instantaneous contact force sensor for the linear actuator.

In another aspect, a needle-free injector as contemplated herein includes a cartridge having a chamber containing a volume of an injectate and an exit port; a plunger positioned slidably coupled to the chamber and positioned to retain the volume of the injectate in the chamber; a drive system coupled to the plunger and operable to drive the plunger into the chamber, thereby propelling the injectate through the exit port; a sensor for monitoring a pressure applied by the plunger to the cartridge; a memory storing a model characterizing a response of the needle-free injector to operation of the drive system and the plunger without the injectate in the cartridge; and a controller coupled to the drive system, controller configured to control operation of the needle-free injector to perform the steps of: operating the plunger at a first rate with the drive system, the first rate different than a piercing rate for the injectate; estimating the response of the needle-free injector with the model during operation of the drive system, thereby providing an estimated response; measuring the response of the needle-free injector with the sensor during operation of the drive system, thereby providing a measured response; while the measured response is within a predetermined threshold of the estimated response, inferring an uncompressed state of the gas bubble and maintaining operation of the plunger at about the first rate; and when the measured response exceeds the predetermined threshold from the estimated response, inferring a compressed state of the gas bubble and changing a velocity of the plunger to the piercing rate.

Figure 10:
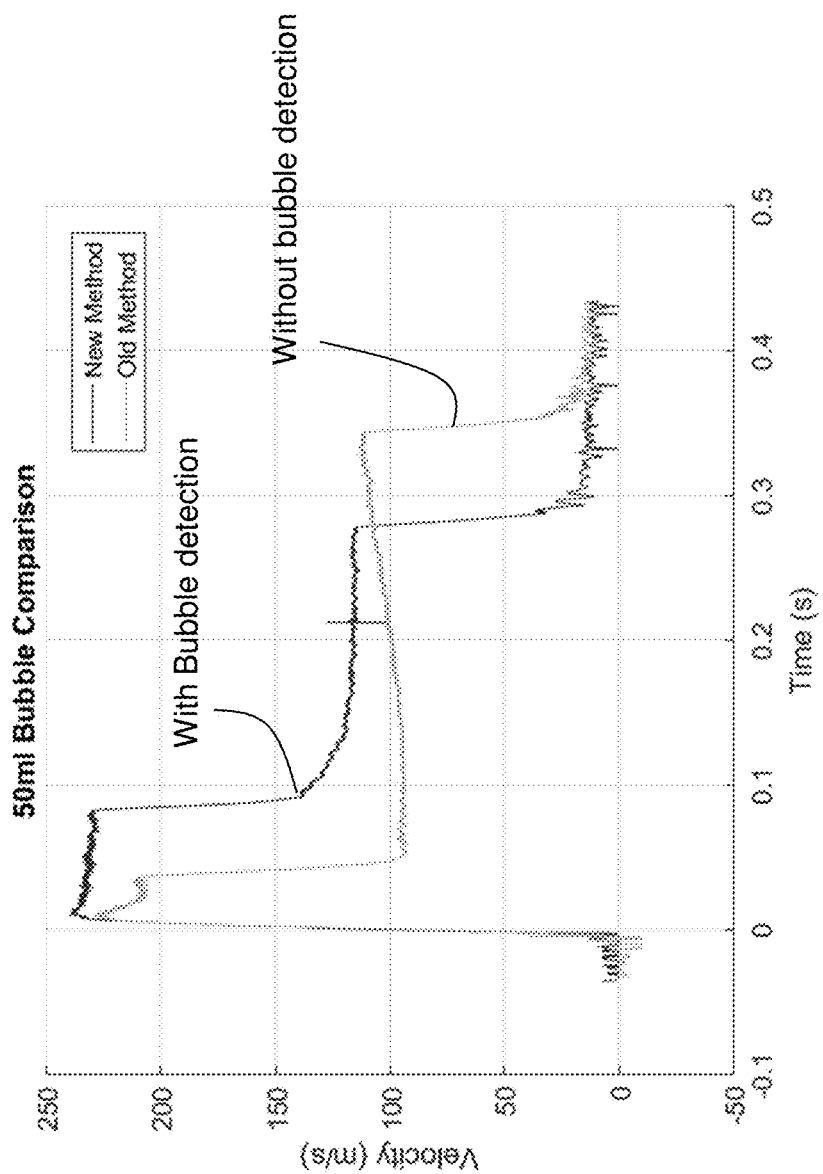
FIG. 10 shows a comparison of two control techniques.

FIG. 10 shows a comparison of two control techniques. In general, an "old method" does not use bubble detection, and a "new method" uses bubble detection as described herein. It can be seen in FIG. 10 that the bubble detection method generally avoids integrator windup errors and associated undershoots and overshoots that extend the time to reach a target velocity for fluid ejection.

Figure 11A:
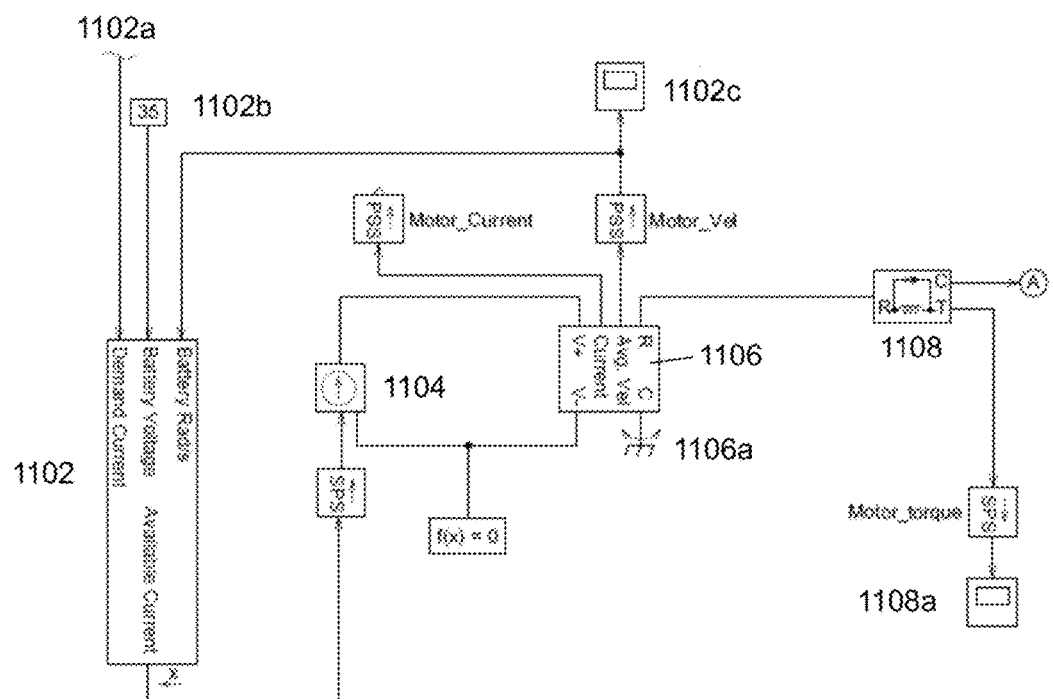
FIGS. 11A and 11B show a model for unloaded operation of an injector powered by a rotary motor.
Figures 11B, 12:
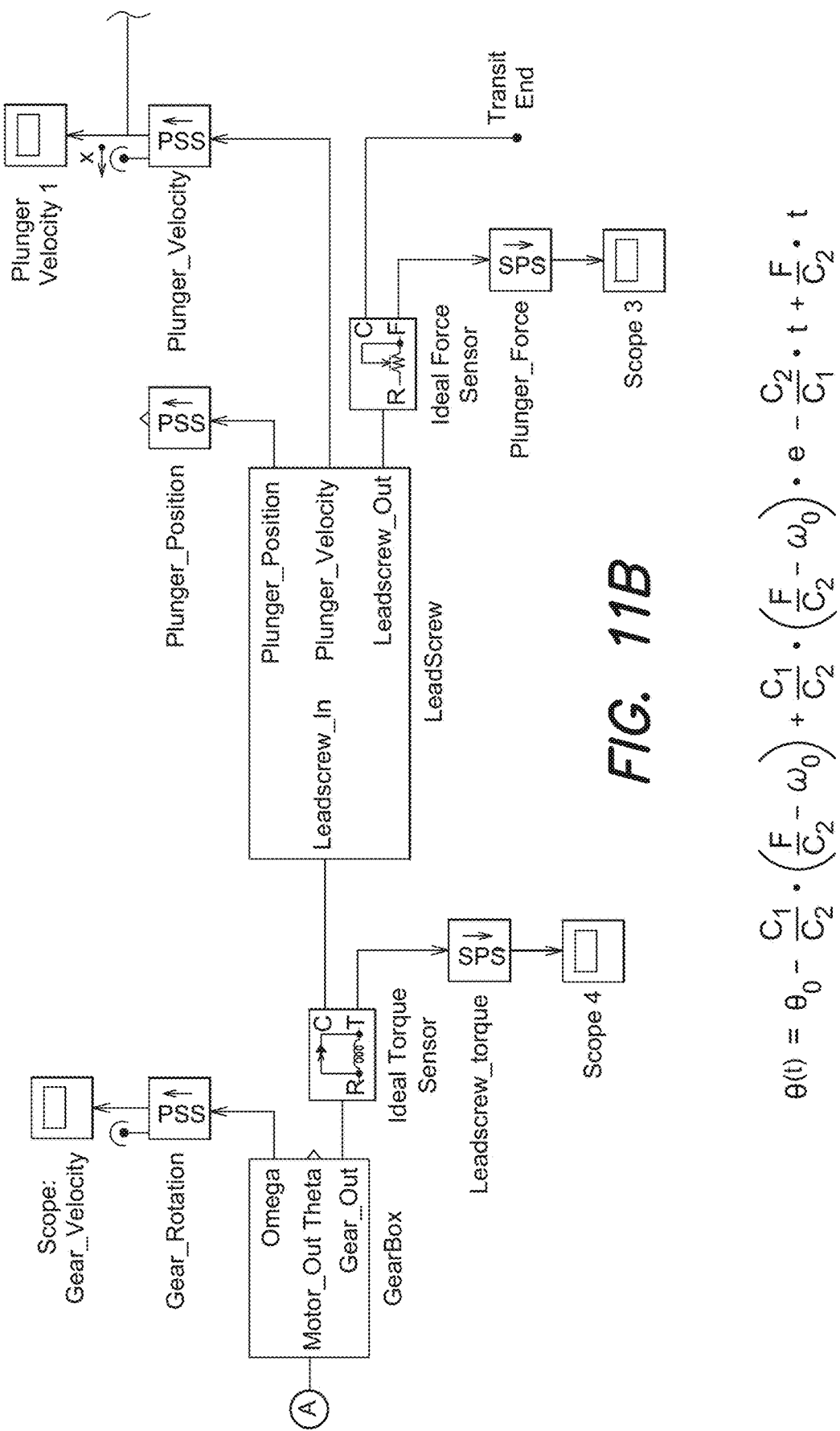
FIG. 12 shows a time continuous equation estimating the operation of the system of FIGS. 11A and 11B.

FIGS. 11A and 11B show a model for unloaded operation of an injector powered by a rotary motor. In general, the model runs alongside the physical device, e.g., on a processor of the device, to estimate an expected behavior of the injector.

FIG. 12 shows a time continuous equation estimating the operation of the system of FIGS. 11A and 11B. When a load such as physical ejection of fluid is imposed on the injector, the behavior of the actual system will deviate from this continuous estimate in a manner that can be detected with a sensor (e.g., for plunger velocity, plunger force, rotary motor speed, or any other detectable variable) and used to determine when an air bubble in a volume of injectate has become compressed.

It will be understood that, while the foregoing techniques may usefully be employed for improved control of a needle-free injector or the like, the insights from this analytic approach—in particular that, before controlling for injectate volume or velocity, a trapped gas bubble or other volume gas within the chamber of an injector should become sufficiently compressed that linear movement of the plunger translates directly and mechanically into displacement of injectate from the device—can also be used in other ways to improve control of a needle-free injector.

For example, in one aspect, the injector may operate at a higher, pre-injection velocity until a volume of fluid is detected at an exit orifice of the injector that indicates adequate gas compression to displace fluid from the chamber. In another aspect, e.g., where the volume of gas forms a discrete, visible bubble at a known location within the chamber, an image of the uncompressed bubble may be used to estimate bubble volume and calculate a suitable, estimated period of initial high speed operation for bubble compression. In another aspect, the back force of the plunger is expected to increase when the bubble becomes compressed. This back force may be directly measured, or measured through a proxy such as a drop in plunger velocity (or an increase in drive current required to maintain a target velocity), and used to detect a suitable time to decrease from a gas compression velocity to a piercing velocity, e.g., when the plunger velocity decreases by a predetermined absolute or relative amount or threshold indicative of a suitable compression state. This threshold may be empirically derived, or otherwise estimated, calculated, or measured prior to an injection in order to provide a target value for detection during an injection. It will be appreciated that any of these techniques may also be varied according to, e.g., the viscosity of an injectate, the diameter of an injection orifice, or any other factors that might affect the amount of bubble compression suitable for transition to a piercing velocity.

In accordance with one or more embodiments, there is provided a needle-free injector. The needle-free injector may include a housing, a cartridge positioned within the housing, a plunger slidably coupled to and disposed within the chamber, and a motor operatively coupled to the plunger that is operable to actuate the plunger in the chamber. The cartridge may include an exit port and a chamber for holding a volume of an injectate. The plunger may be positioned to discharge the volume of the injectate through the exit port when slid within the chamber. The needle-free injector may further include a controller operatively coupled to the motor. The controller may be operable to selectively operate the plunger according to any of a first delivery profile, a second delivery profile, and a third delivery profile.

Figure 13:
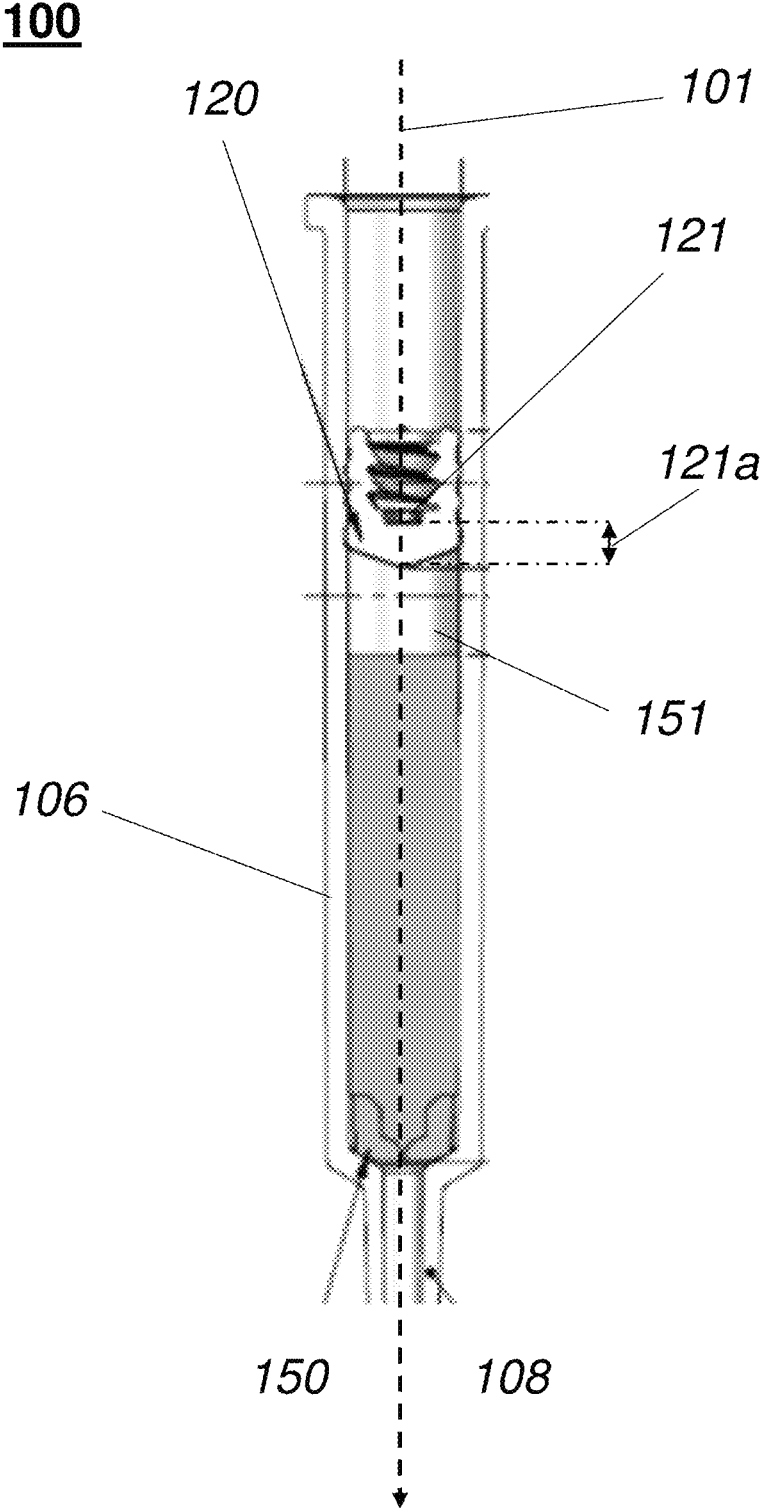
FIG. 13 shows an embodiment of a cartridge and plunger prior to the initiation of an injection, according to one embodiment.

An embodiment of a needle-free injector is illustrated in FIG. 13. With reference to FIG. 13, and in part using the numbering convention of FIG. 1, the needle-free injector 100 includes a chamber 106 having an exit port or nozzle 108 at one end with the axis of flow 101 through the chamber illustrated as the dashed line arrow. The chamber 106 includes an injectate 150 as described herein as well as a volume of gas 151. The volume of gas 151 may form a bubble within or adjacent the injectate 150, or may be distributed throughout or dissolved in the injectate 150 in any number of smaller bubbles, any of which are referred to interchangeably here as a volume of gas or a bubble, unless a more specific meaning is explicitly provided or otherwise clear from the context. The volume of gas 151 may be introduced during the manufacturing process used to enclose the injectate 150 within the chamber 106. This may, for example, be an artifact of the manufacturing process or may be an intentionally included volume of gas specified by a regulatory requirement or operating requirement of the needle-free injector 100. When the needle-free injector 100 is oriented such that the volume of gas 151 rises to the top of the injectate 150 and is adjacent the plunger 120, the volume of gas 151 may form a headspace above the injectate 150.

The needle free injector 100 further includes a plunger 120 positioned within the chamber 106 ahead of the volume of gas 151. The needle free injector 100 further includes a motor (not shown) using a nib 121 operatively coupled to the motor. The nib 121 is configured to be positioned adjacent the plunger 120, and to move along the flow axis 101 when the motor is actuated.

With continued reference to FIG. 13, prior to an injection the plunger 120 may be spaced apart from the nib 121 by a gap 121a. The presence of a gap 121a between the plunger 120 and the nib 121 allows for the acceleration of the nib 121 to a high speed when the motor is actuated, potentially permitting the nib 121 to reach a higher velocity before movement of the plunger 120 is initiated, causing the plunger 120 to move along the flow axis 101 in the chamber 106. After the nib 121 impacts the plunger 120, (or immediately upon activation, for a plunger 120 without a gap 121a), the plunger 120 and the volume of gas 151 within the chamber 106 experience compression, thus pressurizing the injectate 150 within the cartridge 106. Under these conditions, compression of the injectate 150 and the volume of gas 151 in the cartridge 106 may occur rapidly due to the velocity of the plunger 120.

It will be understood that a variety of techniques may be used to measure plunger velocity and load on the plunger 120 and/or motor. For example, the motor may include a rotary encoder that provides a signal corresponding to angular position of the motor. This may be provided as an input to a controller indicative of changes in angular position, which may in turn calculate changes in a linear position of the plunger. At the same time, the controller may provide a drive current to the motor, e.g., according to a drive profile for the injector. The drive current provided by the controller (or in response to a control signal from the controller) may be used to estimate a load on the motor. It will be understood that, while encoder position and drive current are useful and readily available control signals, a variety of other sensors and/or techniques may be used to measure position and load as described herein. For example, the position may be measured optically, electronically, acoustically, and so forth. Similarly, load on the plunger may be measured using force sensors positioned within the device, or by measuring the drive current that is actually output to the motor (as distinguished from the drive current that the controller seeks to provide to the motor).

It will also be understood that a variety of pre-injection control profiles may be used, e.g., where a cartridge of fluid (and the gas) is inserted into an injector, and a nib 121 coupled to the motor is moved into engagement with the plunger 120. In one aspect, the nib 121 may be engaged with the plunger 120 before an injection is initiated. In another aspect, the nib 121 may be positioned close to, but not mechanically engaged with, the plunger 120. For example, in some embodiments, the distance 121a between the nib 121 and the plunger 120 may be about 1 mm to about 10 mm, e.g., about 2 mm to about 8 mm, about 3 mm to about 7 mm, or about 5 mm, e.g., about 1 mm, about 2 mm, about 3 mm, about 4 mm, about 5 mm, about 6 mm, about 7 mm, about 8 mm, about 9mm, or about 10 mm.

As disclosed herein, in one aspect the needle-free injector may operate according to three or more separate delivery profiles for corresponding phases of the injection delivery process: a first delivery profile that initiates an injection, e.g., by accelerating the motor prior to engaging the plunger 120, and detecting initial compression of gas within the cartridge (e.g., a gas compression profile), a second delivery profile that moves rapidly to the initial injection velocity during which the injectate is expelled out of the cartridge at a velocity sufficient for the injectate to penetrate a permeable barrier (e.g., a piercing profile), and a third delivery profile that maintains an injectate velocity sufficient for the delivery of the injectate to a subject (e.g., a delivery profile). The transitions between each of the three profiles may be performed using the controller of the needle free injector. In some embodiments, the transitions between each of the first, second, and third delivery profiles may be a function of a load on the motor and/or plunger. In some examples, the load may be measured, e.g., by receiving a signal from a circuit that measures current supplied to the motor. In another aspect, the load may be inferred, e.g., based on the drive current that the controller requests or outputs for the motor.

In the first delivery profile, the plunger is initially accelerated from zero to a first velocity, typically although not necessarily a high velocity greater than the target velocity within the piercing profile, such as a maximum (rotational) velocity or near-maximum velocity of the motor. This initial acceleration will typically be accompanied by a first spike in current provided to the motor. Once the first velocity is reached, the drive current will decrease to about a steady state current required to drive the plunger at the first velocity. During this phase, a nib coupled to the motor may engage with the plunger as described above, and begin moving the plunger forward in the chamber. However, as gas within the chamber becomes more compressed, the drive current required to maintain a velocity of the plunger will increase. For example, upon compression of the gas within the chamber, e.g., to a state where the gas will not further compress during an injection or to a state where the compressibility of the gas is about equal to the fluid, the load on the motor will become about equal to the load imposed by driving the fluid through an opening for injection. Upon a spike in the drive current (while maintaining a velocity of the plunger) that indicates the contents of the chamber are approaching this state (e.g., indicating compression of the gas beyond a predetermined threshold), the controller may transition to the second delivery profile for ejecting fluid from the injector.

In practice, the first delivery profile use a target velocity at or near a maximum velocity for the motor, or may operate the plunger at a maximum acceleration. In the first delivery profile, when the volume of gas becomes sufficiently compressed, the velocity of the plunger of the needle-free injector may be adjusted according to the second delivery profile for delivery of the injectate to a target. That is, at the detection of compression of the gas, as indicated by the spike in the measured current applied to the motor and/or a decrease in velocity while a substantially constant drive current is applied (e.g., during constant-velocity operation), the operation of the plunger may be transitioned from the first delivery profile to the second delivery profile.

As a significant advantage, measuring the state of compression, and awaiting adequate compression before initiating execution of an injection profile, prevents changes in the state of compression from interfering with control of the injectate velocity during the injection. By detecting the compression of the volume of gas prior to delivery of injectate in this manner, an injection stream can be controlled to more closely reproduce a target injection profile, and artifacts such as integrator wind up and overshoot can be mitigated.

In some embodiments, operating according to the first delivery profile may cause the plunger to operate at a velocity from about 300 m/s to about 500 m/s. For example, the first delivery profile may cause the plunger to operate at a velocity from about 300m/s to about 500 m/s, about 320 m/s to about 480 m/s, about 340 m/s to about 460 m/s, about 360 m/s to about 440 m/s, about 380 m/s to about 420 m/s, or about 400 m/s, e.g., about 300 m/s, about 310 m/s, about 320 m/s, about 330 m/s, about 340 m/s, about 350m/s, about 360 m/s, about 370 m/s, about 380 m/s, about 390 m/s, about 400 m/s, about 410 m/s, about 420 m/s, about 430 m/s, about 440 m/s, about 450 m/s, about 460 m/s, about 470 m/s, about 480 m/s, about 490 m/s, or about 500 m/s, or more than 500 m/s.

Figure 14:
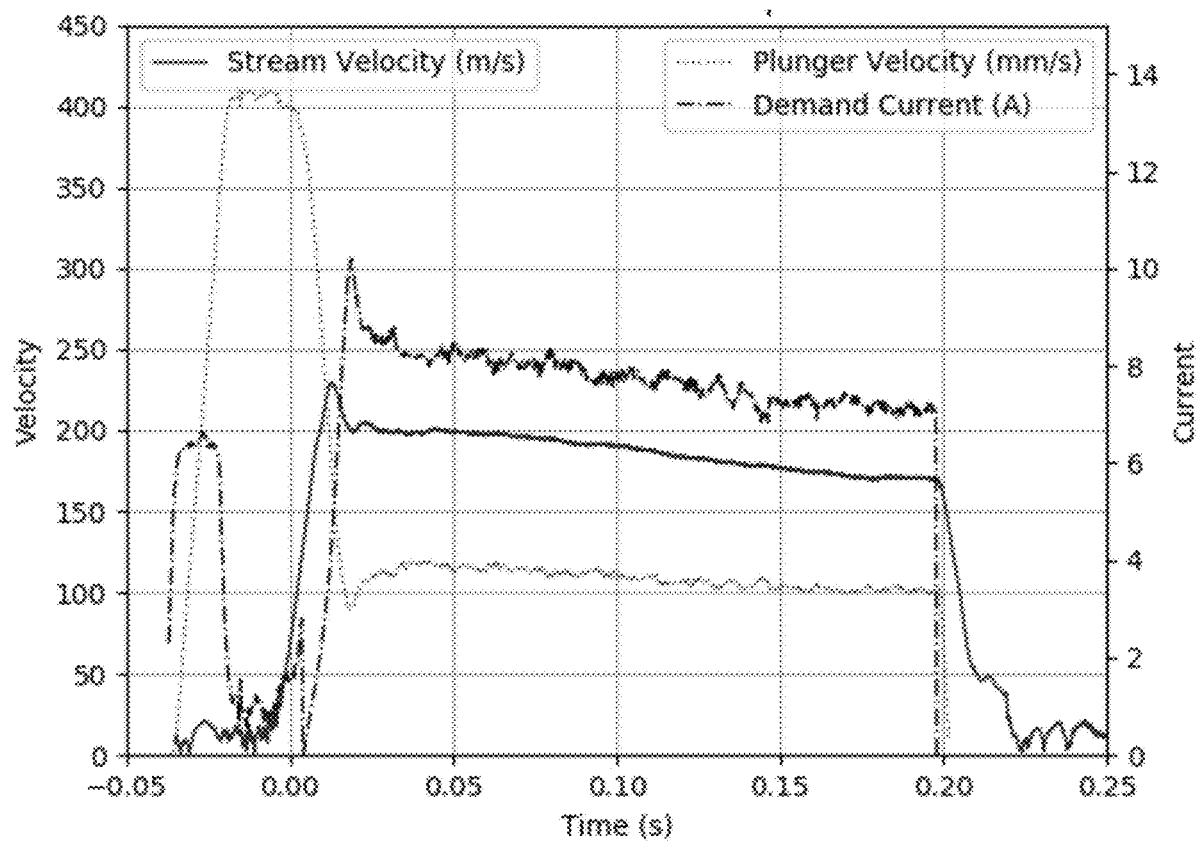
FIG. 14 shows, as a function of time, the current applied to the motor, the plunger velocity, and the injectate velocity for an injection having three delivery profiles, according to one embodiment.

Once the volume of gas has been compressed by the plunger in a manner that can be detected as described herein, the injector may transition to the second delivery profile to produce a high velocity stream of the injectate. As described herein, the second delivery profile targets a high injectate velocity for a short duration, sufficient to produce an injectate velocity capable of penetrating a permeable barrier such as a skin of a subject. This may, for example, including accelerating rapidly to a velocity suitable for piercing. An example of this is illustrated in FIG. 14, where a high plunger velocity is maintained for a short duration and then decreases as the injectate penetrates a permeable barrier, with the decrease in plunger velocity producing a rise in the injectate or stream velocity. It will be noted in FIG. 14 that the drive current may be momentary decreased, such as to nearly zero, to zero, or negative (to brake or provide contrary force on the plunger) before accelerating to the target injection velocity. This can advantageously mitigate an overshoot of the initial target velocity and prevent large, initial swings in the velocity of fluid ejected from the device.

It will be noted that the initial target velocity and the velocity range in this second phase may be significantly less than during the first phase. For example, the injectate velocity produced during operation according to the second delivery profile may be from about 150 m/s to about 250 m/s, e.g., about 150 m/s to about 250 m/s, about 160 m/s to about 240 m/s, about 170 m/s to about 230 m/s, about 180 m/s to about 220 m/s, about 190 m/s to about 210 m/s, or about 200 m/s, e.g., about 150 m/s, about 160 m/s, about 170 m/s, about 180 m/s, about 190 m/s, about 200 m/s, about 210 m/s, about 220 m/s, about 230 m/s, about 240 m/s, or about 250 m/s, or more than 250 m/s. More generally, any velocity or combination of velocities suitable for delivery of injectate in a needle-free injection may be used in the second and third profiles.

As part of the transition from operating according to the first delivery profile to operating according to the second delivery profile, one consideration is the control of the current applied to the motor to avoid overpenetration of the injectate through the permeable barrier. To better control velocity during the second phase, in particular early in the injection with the fluid is piercing tissue, the second delivery profile may be initiated with little or no current applied to the motor. As shown in FIG. 14 (at about five milliseconds along the x axis), the stream velocity may continue to rise even with this momentary decrease in drive current, and the acceleration of the stream velocity can continue to accelerate smoothly as the plunger velocity decreases rapidly toward the target initial velocity for the second phase. In this configuration, the plunger velocity may slow down due to the back pressure received from compression of the volume of gas in the chamber.

Under these conditions, the current applied to the motor, and thus the force applied to the plunger, should increase inversely with the decline in plunger velocity until both the plunger velocity and current applied to the motor reach a steady state condition.

Figure 15A:
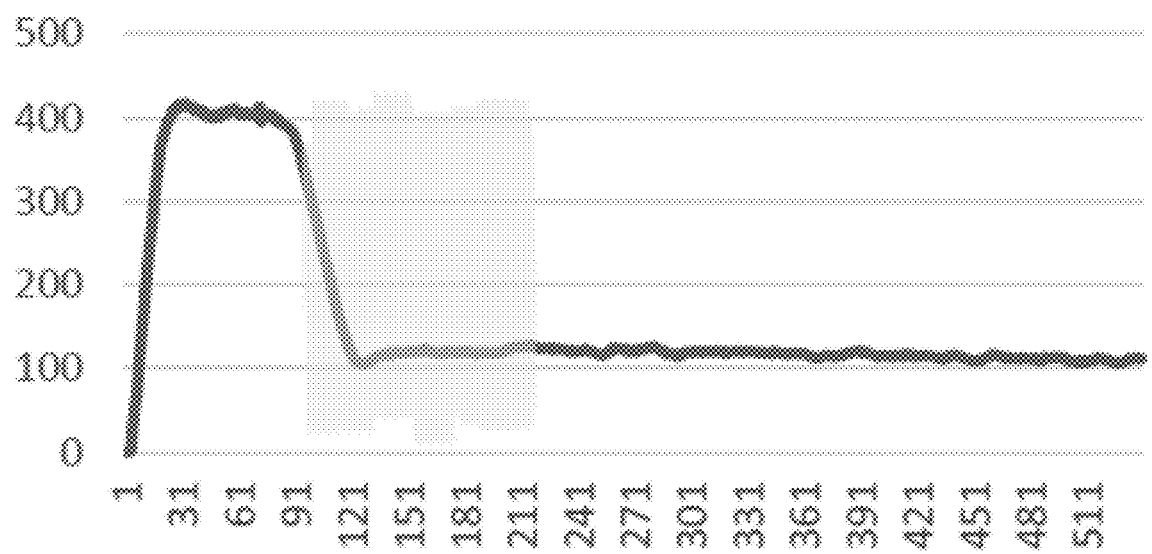
FIGS. 15A-15C show the plunger velocity (FIG. 15A), current applied to the motor (FIG. 15B), and power applied (FIG. 15C) for an injection having three delivery profiles, according to one embodiment.
Figure 15B:
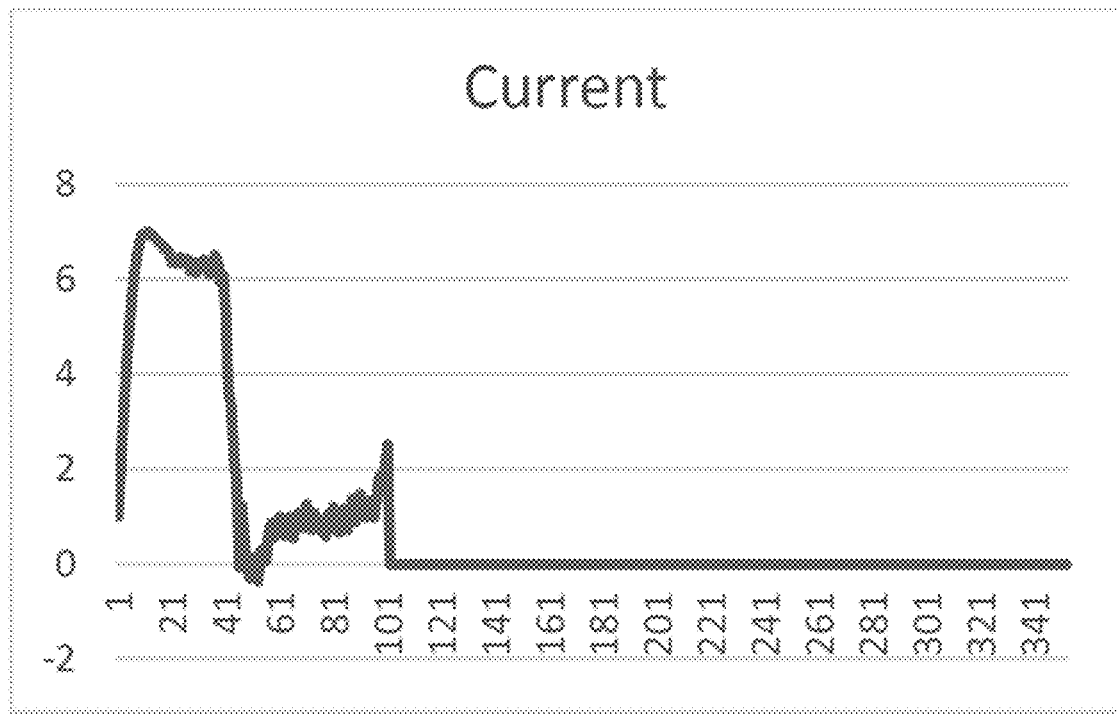
Figure 15C:
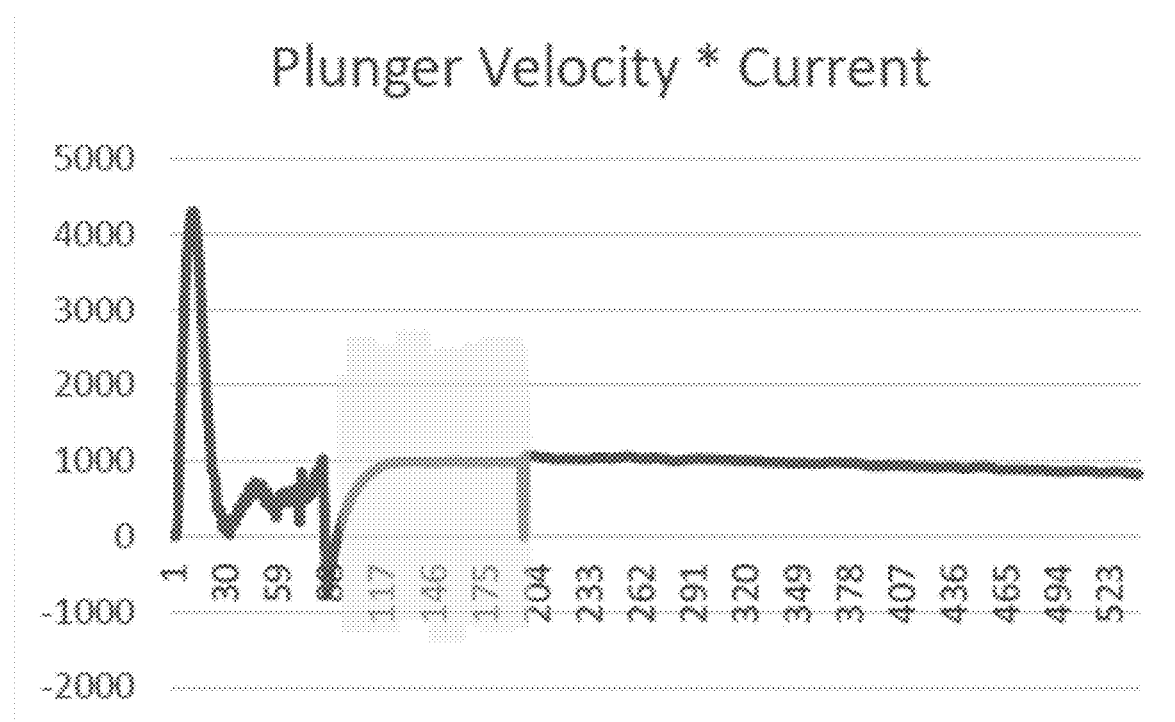

That is, controlling the current and plunger velocity together in a power control mode (illustrated in FIG. 15C where the product of plunger velocity and current is used as a proxy for mechanical power provided to the plunger) permits control of the power into the needle-free injector until the second delivery profile reaches a steady state condition where the plunger velocity, current applied to the motor, and the power supped to the needle free injector are relatively stable for the duration of the injection. For example, the device may use a slowly and monotonically decreasing injection velocity as the injectate is physically delivered from the device.

The foregoing is illustrated in FIGS. 14 and 15A-15C, which illustrate the changes in plunger velocity (FIG. 15A), measured motor current (FIG. 15B), and power measured as the product of plunger velocity and measured motor current (FIG. 15C) as the delivery profiles are changed from the first delivery profile to the second delivery profile and to the third delivery profile after detecting a steady state condition between the measured current and a velocity of the plunger.

In some embodiments, an average velocity of the plunger during operation according to the first delivery profile is greater than an average velocity of the plunger during operation according to the second delivery profile. An example of this is illustrated in FIG. 14. With reference to FIG. 14, the plunger velocity, represented by the dotted line, is highest in the first delivery profile, and upon collision with the plunger in the second delivery profile, drops until a steady state plunger velocity is reached during the third delivery profile.

In some embodiments, operating according to the second delivery profile may cause the plunger to operate at a velocity from about 60 m/s to about 150 m/s. For example, the second delivery profile may cause the plunger to operate at a velocity from about 60 m/s to about 150 m/s, about 70 m/s to about 140 m/s, about 80 m/s to about 130m/s, about 90 m/s to about 120 m/s, or about 110 m/s, e.g., about 60 m/s, about 70 m/s, about 80 m/s, about 90 m/s, about 100 m/s, about 100 m/s, about 120 m/s, about 130 m/s, about 140 m/s, or about 150 m/s, or more than 150 m/s.

Figure 16A:
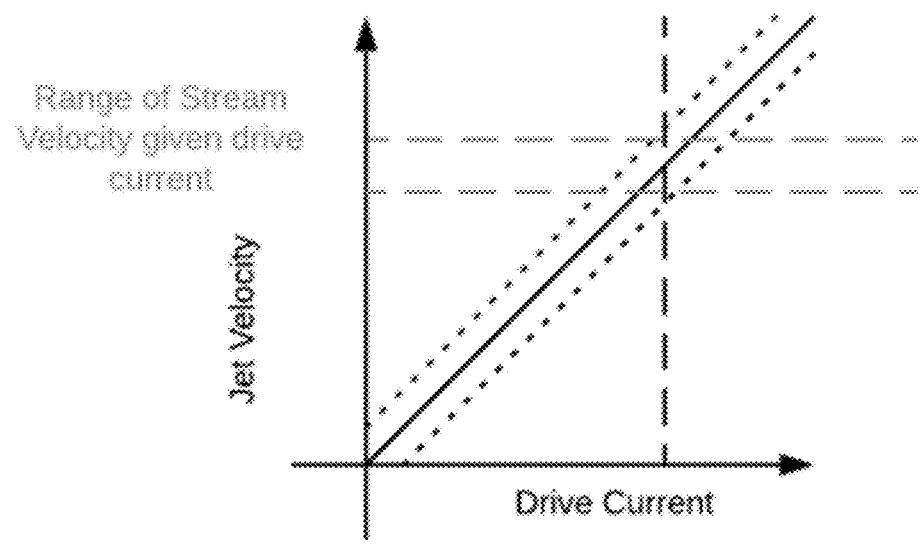
FIGS. 16A-16B show the relationship between injectate velocity and current applied to the motor (FIG. 16A) and plunger velocity (FIG. 16B) for a third delivery profile, according to one embodiment.
Figure 16B:
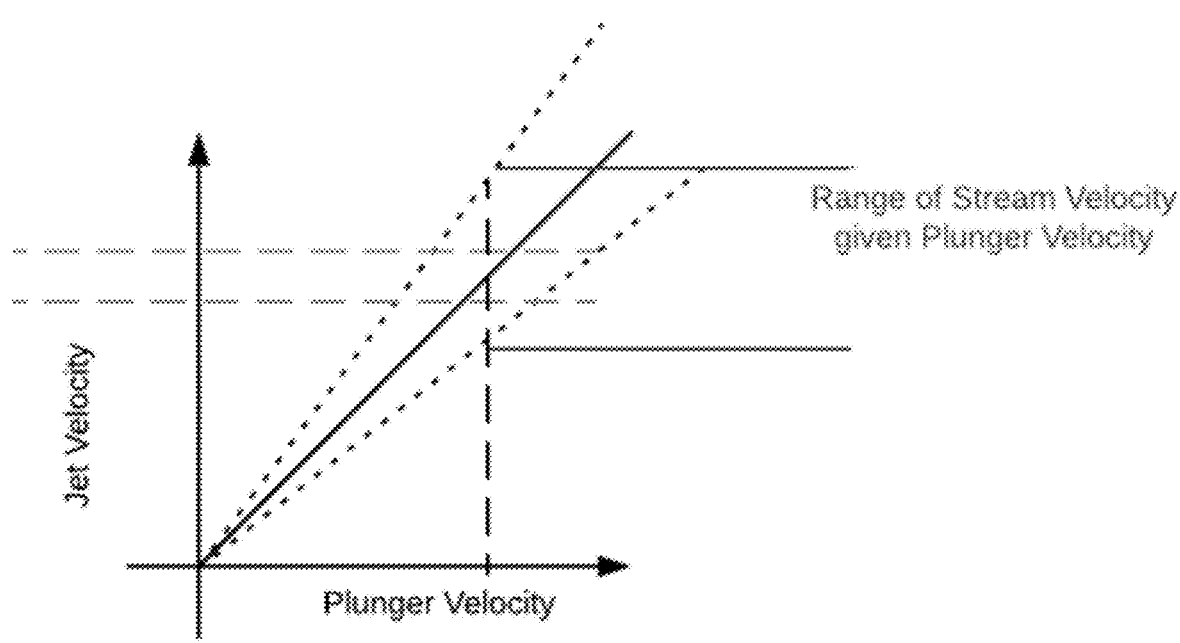

The transition from the second delivery profile to the third delivery profile may occur responsive to detecting a steady state condition between the measured current and a velocity of the plunger until a predetermined volume of the injectate has been delivered from the chamber through the exit port. One consideration of this transition is the reduction of the injectate velocity at a constant deceleration while remaining above a velocity floor. That is, after penetrating the permeable barrier during operation according to the second delivery profile, the velocity of the plunger, and thus the velocity of the injectate, should be maintained during operation according to the third delivery profile to provide for the efficient and complete delivery of an appropriate volume of the injectate into the subject's tissue. To achieve the control and maintenance of the injectate velocity, the third delivery profile may include controlling the plunger velocity, and thus control of the deceleration of the plunger by reducing the current applied to the motor. By performing this deceleration in a slowly and monotonically decreasing pattern, a target velocity for the stream can be maintained in direct proportion to the control current provided. A graphical illustration of the control of the plunger is illustrated in FIGS. 16A and 16B.

In some embodiments, operating according to the third delivery profile may cause the plunger to operate at a velocity from about 80 m/s to about 120 m/s. For example, the second delivery profile may cause the plunger to operate at a velocity from about 80 m/s to about 120 m/s, about 85 m/s to about 115 m/s, about 90 m/s to about 110 m/s, about 90m/s to about 104 m/s, or about 100 m/s, e.g., about 80 m/s, about 85 m/s, about 90 m/s, about 95 m/s, about 100 m/s, about 105 m/s, about 110 m/s, about 115 m/s, or about 120m/s. In one embodiment, the second delivery profile targets a constant velocity (of either the injectate or the plunger) and the third delivery profile targets a slowly and monotonically decreasing velocity. In another aspect, the second delivery profile targets a decreasing velocity (e.g., a slowly and monotonically decreasing velocity) and no third delivery profile is used.

In accordance with one or more embodiments, there is provided a needle-free injector. The needle-free injector may include a plunger positioned to pressurize a fluid and a gas in a cartridge having an exit port and a motor operatively coupled to the plunger. As described herein the plunger may be positioned in contact with the gas in the chamber and the motor may be operable to actuate the plunger in a linear motion along an axis of the cartridge to direct the fluid from the exit port of the cartridge. Actuation of the motor in a first delivery profile may allow the plunger to compress the gas in the chamber and pressurize the injectate in the chamber. The needle free injector, responsive to detecting compression of the gas in the cartridge above a predetermined threshold, can operate in a second delivery profile such as a biphasic profile that includes a piercing phase and a delivery phase. The piercing phase, as described herein, may produce an injectate velocity sufficient to penetrate a permeable barrier but is controlled such that the injectate cannot be delivered deeper into the subject's tissue than is called for. The delivery phase may produce an injectate velocity sufficient to deliver a volume of the injectate to a subject. The delivery phase is further controlled, for example, by controlling the current applied to the motor of the needle free injector, to provide for the complete delivery of an appropriate volume of the injectate into the subject's tissue. In some embodiments, and as described herein, a plunger velocity in the piercing phase decreases as a function of time. The decrease in plunger velocity reduces the resultant injectate velocity to a magnitude that is less likely to result in overpenetration of the injectate into the subject.

The needle-free injector may further include a controller operatively coupled to the motor that may be operable to, responsive to an injection initiation signal, operate the plunger according to the first delivery profile to compress the gas within the cartridge and operate the plunger according to the second delivery profile responsive to detecting a compression of the gas in the cartridge above a predetermined threshold.

In some embodiments, the detecting of the compression of the gas in the cartridge above the predetermined threshold comprises detecting a deviation in a motor current between a free-running drive current predicted by a model and a measured current supplied to the motor. In some embodiments, the detecting of the compression of the gas in the cartridge includes detecting an increase in a motor current above a predetermined threshold for maintaining a velocity of the plunger within the first delivery profile. In some embodiments, detecting the compression of the gas in the cartridge may include detecting a decrease in a velocity of the plunger below a predetermined threshold. In some embodiments, detecting the compression of the gas in the cartridge comprises detecting a concurrent decrease in velocity of the plunger and increase in drive current to the motor. For example, the measured current supplied to the motor may be measured by an encoder operatively coupled to the motor that provides an indication of the rotational position of the motor, and the feedback from the encoder may be used by the controller to actuate the plunger.

In accordance with one or more embodiments, there is provided a method of delivering an injectate using a needle-free injector. The method may include providing a needle-free injector, as described herein. The needle-free injector may include a housing having a cartridge for holding a chamber, a plunger constructed and arranged to direct an injectate from the chamber, and a motor operatively coupled to the plunger. The method may further include, responsive to initiating an injection with the needle-free injector, causing the needle-free injector to operate the plunger according to a first delivery profile, monitor a current applied to the motor during the first delivery profile, transition from the first delivery profile to the second delivery profile responsive to detecting, based at least in part on a spike in the current applied to the motor, compression of a gas in the chamber by the plunger, operate the plunger according to the second delivery profile, transition from the second delivery profile to the third delivery profile responsive to detecting a steady state condition between the measured current and a velocity of the plunger, and to operate the plunger according to the third delivery profile until a predetermined volume of the injectate has been delivered from the chamber through the exit port.

In some embodiments of the method of delivering an injectate, transitioning from the first delivery profile to the second delivery profile may include transitioning from the first delivery profile to the second delivery profile upon detecting a spike in a measured current applied to the motor upon compression of the gas. In some embodiments of the method of delivering an injectate, transitioning from the first delivery profile to the second delivery profile may include decreasing the current applied to the motor to within a range of 0 A to about 10 A.

In some embodiments of the method of delivering an injectate, operating the plunger according to the second delivery profile may include operating the plunger while maintaining the compression of the gas in the chamber. In some embodiments of the method of delivering an injectate, operating the plunger according to the second delivery profile may result in the injectate velocity being sufficient to penetrate a permeable barrier. For example, as described herein, the permeable barrier may be the skin of a subject.

In some embodiments of the method of delivering an injectate, operating the plunger in the third delivery profile may include adjusting the velocity of the plunger as the injectate is delivered. For example, during delivery of the injectate, the third delivery profile may be configured to decrease the velocity of the plunger to reduce the velocity of the injectate.

In accordance with one or more embodiments, there is provided a method of facilitating needle-free injection of an injectate. The method may include providing a needle-free injector as described herein, such as a needle-free injector including a motor operatively coupled to a plunger and a controller. The controller provided with the needle-free injector may be a controller as described herein, and may be operable to operate the plunger in a first delivery profile, monitor a current applied to the motor during the first delivery profile, transition from the first delivery profile to the second delivery profile responsive to detecting, based at least in part on a spike in the current applied to the motor, compression of a gas in the chamber by the plunger, operate the plunger in the second delivery profile, transition from the second delivery profile to the third delivery profile responsive to detecting a steady state condition between the measured current and a velocity of the plunger, and to operate the plunger according to the third delivery profile until a predetermined volume of the injectate has been delivered from the chamber through the exit port.

In some embodiments of the method of facilitating, the method may further include providing instructions to a user for loading a cartridge of the injectate into the needle-free injector. In some embodiments of the method of facilitating, the method may further include providing instructions to a user for operating the needle-free injector.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions.

Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it may be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context. Absent an explicit indication to the contrary, the disclosed steps may be modified, supplemented, omitted, and/or re-ordered without departing from the scope of this disclosure.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A needle-free injector, comprising:
   a plunger positioned to pressurize a fluid and a gas in a cartridge having an exit port;
   a motor operatively coupled to the plunger, the motor operable to actuate the plunger in a linear motion along an axis of the cartridge to direct the fluid from the cartridge; and
   a controller operatively coupled to the motor, the controller operable to, responsive to an injection initiation signal, operate the plunger according to a first delivery profile to compress the gas within the cartridge and operate the plunger according to a second delivery profile responsive to detecting a compression of the gas in the cartridge above a predetermined threshold, wherein detecting the compression of the gas in the cartridge comprises detecting a concurrent decrease in velocity of the plunger and increase in drive current to the motor.

2. The needle-free injector of claim 1, wherein detecting the compression of the gas in the cartridge alternatively comprises detecting a deviation in a motor current between a free-running drive current predicted by a model and a measured current supplied to the motor.

3. The needle-free injector of claim 1, wherein detecting the compression of the gas in the cartridge alternatively comprises detecting an increase in a motor current above a predetermined threshold for maintaining the velocity of the plunger within the first delivery profile.

4. The needle-free injector of claim 1, wherein detecting the compression of the gas in the cartridge alternatively comprises detecting a decrease in the velocity of the plunger below a predetermined threshold.

5. The needle-free injector of claim 1, wherein the controller actuates the plunger responsive to feedback from an encoder operatively coupled to the motor.

6. The needle-free injector of claim 1, wherein the first delivery profile has a first target velocity greater than a second target velocity of the second delivery profile.

7. The needle-free injector of claim 6, wherein the second delivery profile is a biphasic profile comprising a piercing phase and a delivery phase.

8. The needle-free injector of claim 7, wherein a plunger velocity in the piercing phase decreases as a function of time.

9. The needle-free injector of claim 1, wherein the fluid includes at least one of an injectable pharmaceutical, an injectable nutraceutical formulation, and a high viscosity biologic formulation.

10. The needle-free injector of claim 1, wherein a plunger velocity of the second delivery profile produces an injectate velocity of the fluid from the exit port sufficient for the fluid to penetrate a skin of a human subject.

11. A needle-free injector, comprising:
    a plunger positioned to pressurize a fluid and a gas in a cartridge having an exit port;

a motor operatively coupled to the plunger, the motor operable to actuate the plunger in a linear motion along an axis of the cartridge to direct the fluid from the cartridge; and a controller operatively coupled to the motor, the controller operable to, responsive to an injection initiation signal, operate the plunger according to a first delivery profile to compress the gas within the cartridge and operate the plunger according to a second delivery profile responsive to detecting a compression of the gas in the cartridge above a predetermined threshold, wherein the first delivery profile has a first target velocity greater than a second target velocity of the second delivery profile.

12. The needle-free injector of claim 11, wherein a plunger velocity of the second delivery profile produces an injectate velocity of the fluid from the exit port sufficient for the fluid to penetrate a skin of a human subject.

13. The needle-free injector of claim 12, wherein detecting the compression of the gas in the cartridge above the predetermined threshold comprises detecting a deviation in a motor current between a free-running drive current predicted by a model and a measured current supplied to the motor.

14. The needle-free injector of claim 12, wherein detecting the compression of the gas in the cartridge comprises detecting an increase in a motor current above a predetermined threshold for maintaining a velocity of the plunger within the first delivery profile.

15. The needle-free injector of claim 12, wherein detecting the compression of the gas in the cartridge alternatively comprises detecting a decrease in a velocity of the plunger below a predetermined threshold.

16. The needle-free injector of claim 12, wherein the controller actuates the plunger responsive to feedback from an encoder operatively coupled to the motor.

17. The needle-free injector of claim 11 wherein the second delivery profile is a biphasic profile comprising a piercing phase and a delivery phase.

18. The needle-free injector of claim 17, wherein a plunger velocity in the piercing phase decreases as a function of time.

19. The needle-free injector of claim 12, wherein the fluid includes an injectable pharmaceutical.

20. The needle-free injector of claim 12, wherein the fluid includes a high viscosity biologic formulation.

* * * * *